(12) United States Patent
Gao

(10) Patent No.: US 9,008,977 B2
(45) Date of Patent: Apr. 14, 2015

(54) DETERMINING FLUID DENSITY

(75) Inventor: Li Gao, Katy, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 762 days.

(21) Appl. No.: 13/320,311

(22) PCT Filed: May 20, 2009

(86) PCT No.: PCT/US2009/044607
§ 371 (c)(1),
(2), (4) Date: Nov. 14, 2011

(87) PCT Pub. No.: WO2010/134911
PCT Pub. Date: Nov. 25, 2010

(65) Prior Publication Data
US 2012/0072128 A1    Mar. 22, 2012

(51) Int. Cl.
*G01N 9/00* (2006.01)
*G01H 1/00* (2006.01)
(Continued)

(52) U.S. Cl.
CPC ............... *G01N 35/00* (2013.01); *G06F 19/00* (2013.01); *G01H 1/00* (2013.01); *G01H 3/00* (2013.01); *G06F 17/40* (2013.01); *G01N 9/00* (2013.01)

(58) Field of Classification Search
CPC ........... G01D 7/00; G01D 9/00; G01D 21/00; G01F 1/00; G01F 3/00; G01F 15/00; G01F 15/02; G01F 22/00; G01H 1/00; G01H 1/04; G01H 1/06; G01H 1/12; G01H 1/14; G01H 3/00; G01H 3/04; G01H 3/06; G01H 11/00; G01H 11/02; G01H 11/04; G01H 13/00; G01H 17/00; G01N 9/00; G01N 9/002; G01N 9/32; G01N 29/00; G01N 29/02; G01N 29/036; G06F 11/00; G06F 11/32; G06F 11/34; G06F 15/00; G06F 15/56; G06F 17/00; G06F 17/10; G06F 17/40; G06F 19/00
USPC ................. 73/1.01, 1.82, 23.2, 24.01, 24.05, 73/30.01, 32 R, 32 A, 152.01, 152.02, 73/152.03, 152.54, 152.55, 152.58, 432.1, 73/570, 579, 584, 865.8, 865.9, 866.3; 137/551; 702/1, 22, 23, 33, 50, 54, 85, 702/104, 127, 137, 182, 187, 189; 708/100, 708/105, 200
See application file for complete search history.

(56) References Cited

U.S. PATENT DOCUMENTS 2,635,462 A * 4/1953 Poole et al. .................... 73/32 A
2,956,431 A * 10/1960 Westerheim .................. 73/32 R
(Continued)

OTHER PUBLICATIONS

Intellectual Property Office, Examination Report under Section 18(3) for application No. GB1118895.0, which is the UK application that corresponds to the instant application, dated Mar. 11, 2013.
(Continued)

Primary Examiner — Edward Cosimano
(74) Attorney, Agent, or Firm — Howard L. Speight, PLLC

(57) ABSTRACT

The density of a fluid is determined using a vibratory resonant densitometer in an environment. The densitometer includes a tubular sample cavity and other densitometer parts. The method includes measuring a plurality of parameters characterizing the environment. The method further includes adjusting a model of the sample cavity using the measured parameters. The method further includes receiving a sample fluid into the sample cavity. The method further includes vibrating the sample cavity to obtain a vibration signal. The method further includes calculating the density of the sample fluid using the model and the vibration signal.

17 Claims, 21 Drawing Sheets

(51) Int. Cl.
  *G01H 3/00* (2006.01)
  *G06F 17/40* (2006.01)
  *G06F 19/00* (2011.01)
  *G01N 35/00* (2006.01)

(56) References Cited

U.S. PATENT DOCUMENTS

| | | | | |
|---|---|---|---|---|
| 3,113,455 | A | * | 12/1963 | Sloan et al. ............... 73/152.18 |
| 3,516,283 | A | * | 6/1970 | Abbotts ..................... 73/24.05 |
| 3,677,067 | A | | 7/1972 | Miller et al. |
| 3,706,220 | A | | 12/1972 | Miller |
| 3,738,155 | A | | 6/1973 | Miller |
| 3,741,000 | A | | 6/1973 | Miller |
| 3,805,592 | A | | 4/1974 | Miller et al. |
| 3,878,374 | A | | 4/1975 | Schlatter |
| 4,084,425 | A | | 4/1978 | Bae |
| 4,193,291 | A | | 3/1980 | Lynnworth |
| 4,491,009 | A | * | 1/1985 | Ruesch ..................... 73/32 A |
| 6,378,364 | B1 | | 4/2002 | Pelletier et al. |
| 6,688,176 | B2 | | 2/2004 | Storm, Jr. et al. |
| 6,912,904 | B2 | | 7/2005 | Storm, Jr. et al. |
| 7,058,549 | B2 | | 6/2006 | Gysling et al. |

OTHER PUBLICATIONS

IP Australia, Deed of Letters Patent 20093463654, which is the AU application that corresponds to the instant application.

IP Australia, Discovery House, Phillip ACT 2606, PO Box 200, Woden ACT 2606, Australia, Notice of Sealing for AU patent No. 2009346364, which is the AU application that corresponds to the instant application, dated Apr. 4, 2013.

Intellectual Property Office, Patents Act 1977: Examination Report under Section 18(3), Nov. 27, 2012. Concept House, Cardiff Road, Newport, South Wales, NP10 8QQ, Great Britain.

IP Australia, Corrected Claims as Accepted, downloaded from http://pericles.ipaustralia.gov.au/ols/auspat/applicationDetails.do?applicationNo=2009346364, Jan. 10, 2013, Discovery House, Phillip ACT 2606, Australia.

IP Australia, Letter apologizing for error in specification published at time of acceptance, Jan. 10, 2013, Discovery House, Phillip ACT 2606, Australia.

IP Australia, Notice of Acceptance [Corrected], Dec. 5, 2012, Discovery House, Phillip ACT 2806, Australia.

IP Australia, Notice of Acceptance, Dec. 5, 2012, Discovery House, Phillip ACT 2806, Australia.

Australian Government, IP Australia, Examiner's first report on patent application No. 2009346364 (which is the Australian patent application that corresponds to the instant application), Dec. 16, 2011.

Grant, D.A., "The Effect of Rotary Intertia and Shear Deformation on the Frequency and Normal Mode Equations of Uniform Beams Carrying a Concentrated Mass," Journal of Sound and Vibration (1978) 57(3), 357-365.

PCT/US09/44607, International Preliminary Report on Patentability, Oct. 3, 2011.

PCT/US09/44607, International Search Report and Written Opinion of the International Searching Authority, Jul. 13, 2009.

Salem, Jonathan A., et al., "Strength, Fatigue, and Fracture Toughness of Ti-6AI-4V Liner From a Composite Over-Wrapped Pressure Vessel," NASA/TM-2008-215147 (Mar. 2008) 1-26.

Timoshenko, S., Vibration Problems in Engineering, 414-423 (John Wiley & Sons 1974).

Young, Warren C., Roark's Formulas for Stress and Strain, 683-685 (McGraw-Hill Companies 2002).

* cited by examiner

DETERMINING FLUID DENSITY

BACKGROUND

It is often important to be able to measure the density of fluids in the oil field or in other contexts. Techniques and equipment for making such measurements are described in U.S. Pat. Nos. 6,378,364; 6,688,176; and 6,912,904, which are all assigned to the assignee of the present application. The '176 patent describes a curve-fitting approach for measuring fluid density.

DETAILED DESCRIPTION

Apparatus/Tube/Sensors

Figure 1:
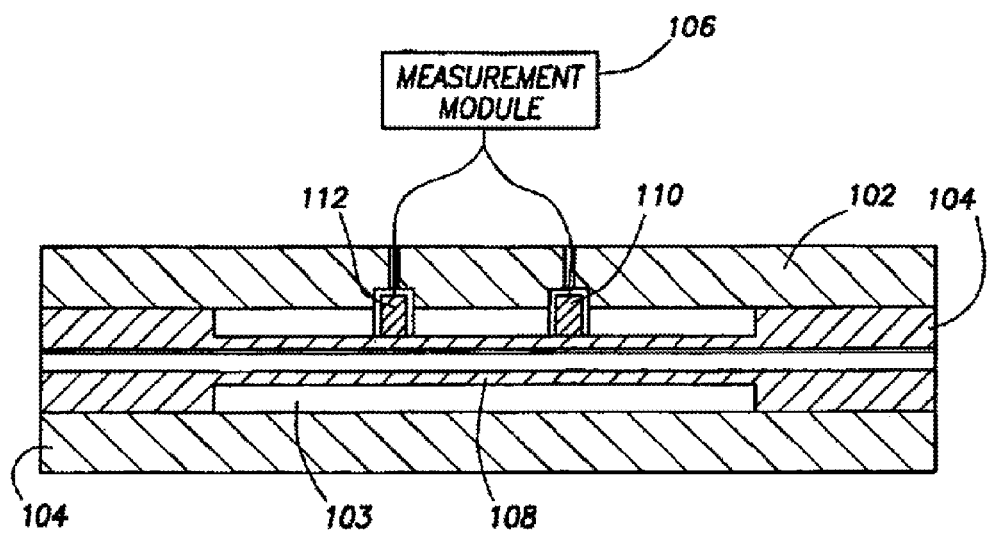
FIG. 1 shows one embodiment of a densitometer according to the present invention.

Referring now to FIG. 1, one embodiment of a device for measuring density and viscosity of a flowing fluid, generally includes a rigid housing 102, two bulkheads 104, a single flow tube 108, a single vibration source 110, a single vibration detector 112, and a measurement module 106. The rigid housing 102 surrounds and protects a volume 103 through which the flow tube 108 passes and reduces the response to vibrations not associated with particular vibratory modes of the flow tube 108. The bulkheads 104 seal the volume and secure the flow tube 108 within that volume. The volume 103 preferably contains air, a vacuum or a relatively inert gas such as nitrogen or argon. If gasses are used, then they are preferably at atmospheric pressure when the device is at room temperature.

The rigid housing 102, bulkheads 104, and flow tube 108 are preferably made from material in a configuration that can withstand pressures of more than 20,000 psi (pounds per square inch) at temperatures of 250° C. or more. Two examples of suitable materials are Titanium and Hastaloy-HA276C. Preferably, the bulkheads 104 and the flow tube 108 are constructed from the same piece of material, with the bulkheads 104 being regions of larger diameter on either end of the tube 108. Alternatively, the flow tube 108 may be welded to the bulkheads 104, or otherwise attached. The flow tube 108 may also be secured to the rigid housing 102 by o-rings or other types of elastomeric means. Preferably, the rigid housing 102, bulkheads 104, and the flow tube 108 are constructed from the same material in order to alleviate thermally induced stresses when the system is in thermal equilibrium.

The flow tube 108 is preferably straight, as this reduces any tendencies for plugging and erosion by materials passing through the flow tube 108. However, it is recognized that bent tubes of various shapes, including "U"-shaped tubes, may provide greater measurement sensitivities. Contemplated dimensions for the embodiment of FIG. 1 are shown in Table 1:

TABLE 1

|  | Flow Tube | Bulkhead | Housing |
| --- | --- | --- | --- |
| Length | 6" | 2" | 10" |
| Outer Diam | 0.304" | 1.5" | 2" |
| Inner Diam | 0.219" | — | ~1.5" |

However, it is noted that other dimensions may be used without departing from the scope of the invention.

Figure 2:
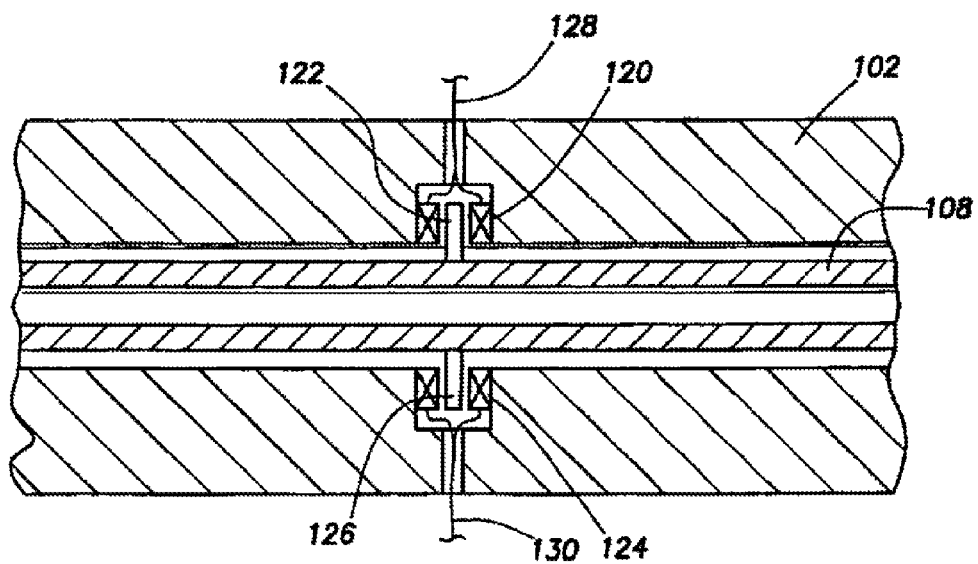
FIG. 2 shows another embodiment of a densitometer according to the present invention.
Figure 3A:
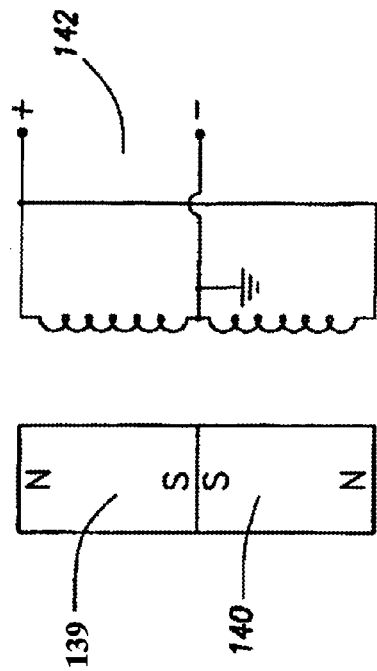
FIG. 3A is an electrical schematic depicting one embodiment of the receiver arrangement in accordance with the present invention.
Figure 3:
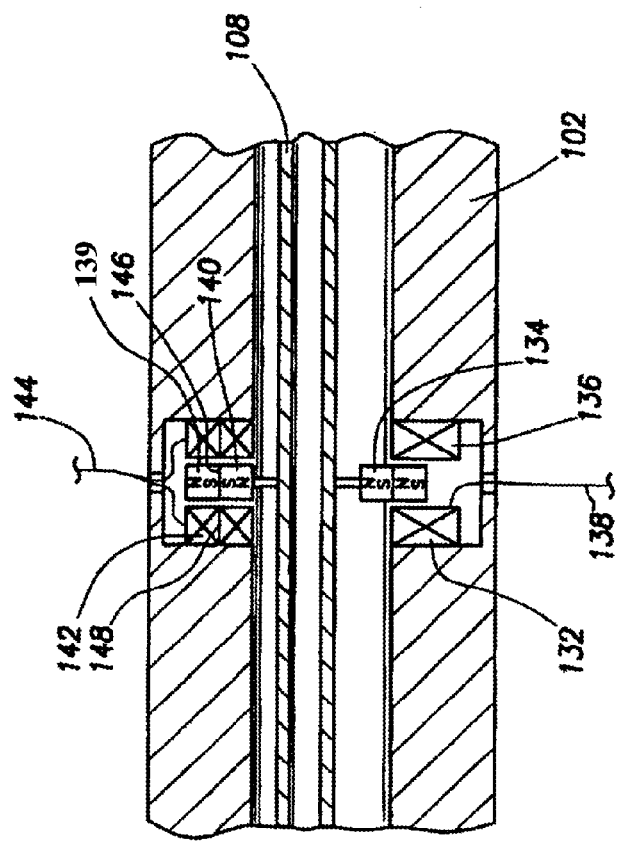
FIG. 3 shows one embodiment of the receiver and transmitter arrangements in accordance with the present invention.

As described above, attached to the flow tube 108 are a vibration source 110 and a vibration detector 112. The vibration source 110 and vibration detector 112 may be located side by side as shown in FIG. 1 or, alternatively located on opposite sides of the flow tube 108 at a point halfway between the bulkheads 104, as shown in FIGS. 2 and 3. Other source/detector configurations are also contemplated.

Now referring to FIG. 2, one embodiment of the present invention is illustrated comprising a flow tube 108, two toroidal coils 120, 124 connected to the housing 102, and two ferrous rods 122, 126 connected to the flow tube 108. The coils 120, 124 may also incorporate a ferrous core to form a more effective electromagnet. One coil 120 is connected by electrical leads 128 to a transmitter (not shown). Application of an alternating current to the coil 120 exerts an electromagnetic force on the rod 122, which causes the rod 122 to translate linearly, therefore imparting a vibration on the tube 108. The other coil 124 is connected by leads 130 to a receiver (not shown). The vibration in the tube 108 moves the rod 126 within the coil 124, therefore creating a voltage to generate at the leads 130 that is monitored by the receiver.

The above described configuration has the advantage of using the lightest weight ferrous rod 122, 126 and yields higher sensitivity to density changes than similar applications with heavier rods. The disadvantages are that more power is required to drive the tube and the receiver is not as effective as desired. The effectiveness of the receiver may be limited by interference created by the interaction of the magnetic fields of the transmitter and receiver.

Now referring to FIG. 3, a more effective vibration source 132 is illustrated, comprising a magnet 134 secured to the flow tube 108, and a single coil winding 136 secured to the housing 102. The coil 136 is connected by leads 138 to a transmitter (not shown). The coil 136 is mounted toward the outer extreme of the magnet 134 (this is exaggerated in the figure for clarity). The precise mounting location of the coil 136 is empirically determined by maximizing the vibration force imparted upon the flow tube 108. Applying an alternating current to the coil 136 causes a resulting electromagnetic force that vibrates the flow tube 108.

Still in reference to FIG. 3, the preferred embodiment of the vibration detector is illustrated comprising two magnets 139, 140 secured to the vibrating flow tube 108, and a dual coil winding 142 secured to the housing 102. The dual coil 142 is connected by leads 144 to a receiver (not shown). The symmetry axes of the magnets 139, 140 and dual coil 142 are aligned and the magnets 139, 140 are arranged such that their magnetic fields repel. The dual coil 142 is preferably composed of two identical coils mounted end-to-end with symmetry axes aligned and electrically connected in series. A schematic of the dual coil 142 is presented in FIG. 3A. The plane 146 defined by the interface of the magnets 139, 140 is aligned with plane 148 defined by the intersection of the opposing coil windings of the dual coil 142 as shown in FIG. 3. The coils are connected so as to be phased in such a way that minimal or no voltage is generated at the leads 144 if the coils are placed in a uniform magnetic field (such as that induced by current flow in the nearby vibration source). However, the coils do respond to movement of the opposed magnet pair. Applying a vibration to the flow tube 108 causes a voltage to be generated at the leads 144 of the dual coil 142.

The unique arrangement of the vibration detector magnets 139, 140 acts to minimize the magnetic field created by the vibration detector as well as the effects of the magnetic field created by the vibration source. The net effect of this arrangement is to decrease the interference created in the signal produced by the vibration detector, which allows variations in the vibration of the flow tube 108 to be more accurately and reliably detected.

It is noted that in both embodiments, the vibration sources and vibration detectors are preferably mounted near an antinode (point of maximum displacement from the equilibrium position) of the mode of vibration they are intended to excite and monitor. It is contemplated that more than one mode of vibration may be employed (e.g. the vibration source may switch between multiple frequencies to obtain information from higher resonance harmonic frequencies). The vibration sources and detectors are preferably positioned so as to be near antinodes for each of the vibration modes of interest.

The locations of nodes (points of zero vibrational amplitude) and antinodes are determined by the vibration modes and by the mounting of the tube 108. For example, for a tube having length L with both ends rigidly fixed, for the first mode of vibration (the fundamental mode), the antinode lies exactly at the center of the tube at 0.5 L For the second mode of vibration, the node is at 0.5 L. But there are two antinodes: one at approximately 0.29 L, the other at approximately 0.71 L.

It will be understood that the vibration detector could be another type of detector other than that shown in FIGS. 1-3. For example, a laser vibrometer could be used as the vibration detector. Instead of a voice coil for signal pick up, Giant Magneto-Resistance (GMR) sensors can be used. Capacitive displacement sensor may also be used.

Measurement Module

Figure 4:
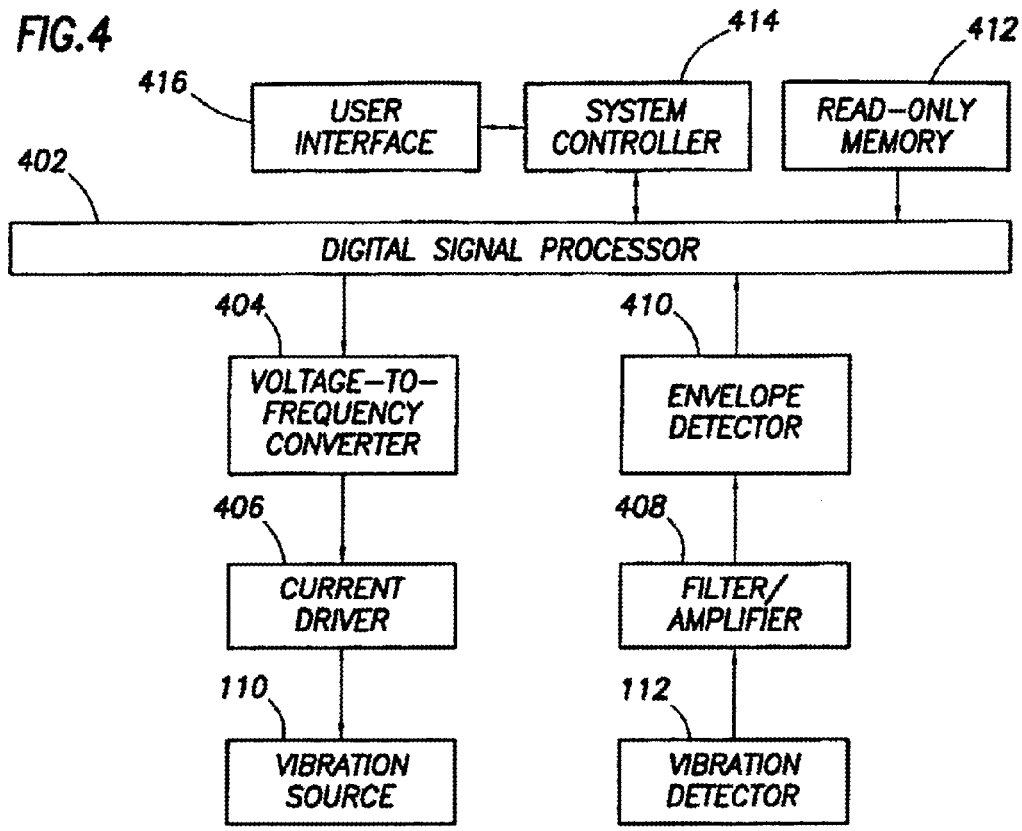
FIG. 4 shows an exemplary measurement module.

Referring now to FIG. 4, one embodiment of the measurement module generally includes a digital signal processor 402, voltage-to-frequency converter 404, current driver 406, filter/amplifier 408, amplitude detector 410, and a read-only memory (ROM) 412. The digital signal processor 402 may be configured and controlled by a system controller 414 that operates in response to actions of the user on the user interface 416. The system controller 414 preferably also retrieves measurements from the digital signal processor 402 and provides them to the user interface 416 for display to the user. The measurement module can be powered by a downhole battery, a downhole power generator, or via power supplied from the surface. Parts of the measurement module may be at the surface. For example, the system controller may be at the surface.

The digital signal processor 402 preferably executes a set of software instructions stored in ROM 412. Typically, configuration parameters are provided by the software programmer so that some aspects of the digital signal processor's operation can be customized by the user via interface 416 and system controller 414. Preferably, the set of software instructions causes the digital signal processor 402 to perform density measurements according to one or more of the methods detailed further below. The digital signal processor preferably includes digital to analog (D/A) and analog to digital (A/D) conversion circuitry for providing and receiving analog signals to off-chip components. Generally, most on-chip operations by the digital signal processor are performed on digital signals.

In performing one of the methods described further below, the digital signal processor 402 provides a voltage signal to the voltage-to-frequency converter 404. The voltage-to-frequency converter 404 produces a frequency signal having a frequency proportional to the input voltage. The current driver 406 receives this frequency signal and amplifies it to drive the vibration source 110. The vibration source 110 causes the flow tube to vibrate, and the vibrations are detected by vibration detector 112. A filter/amplifier 408 receives the detection signal from vibration detector 112 and provides some filtering and amplification of the detection signal before passing the detection signal to the amplitude detector 410. The filter/amplifier 408 serves to isolate the vibration detector 112 from the amplitude detector 410 to prevent the amplitude detector 410 from electrically loading the vibration detector 112 and thereby adversely affecting the detection sensitivity. The amplitude detector 410 produces a voltage signal indicative of the amplitude of the detection signal. The digital signal processor 402 measures this voltage signal, and is thereby able to determine a vibration amplitude for the chosen vibration frequency.

Figure 5:
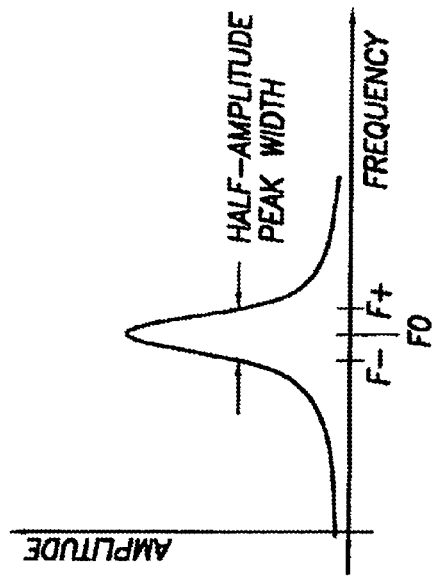
FIG. 5 shows a graph of an exemplary resonance peak.

The measurement module employs the vibration source 110 and vibration detector 112 to locate and characterize the resonance frequencies of the flow tube 108. Several different methods are contemplated. In a first method, the measurement module causes the vibration source 110 to perform a frequency "sweep" across the range of interest, and record the amplitude readings from the vibration detector 112 as a function of the frequency. As shown in FIG. 5, a plot of the vibration amplitude versus frequency will show a peak at the resonance frequency $f_0$. The resonance frequency can be converted to a density measurement, and the shape of the peak may yield additional information such as viscosity and multiple phase information.

Figure 6:
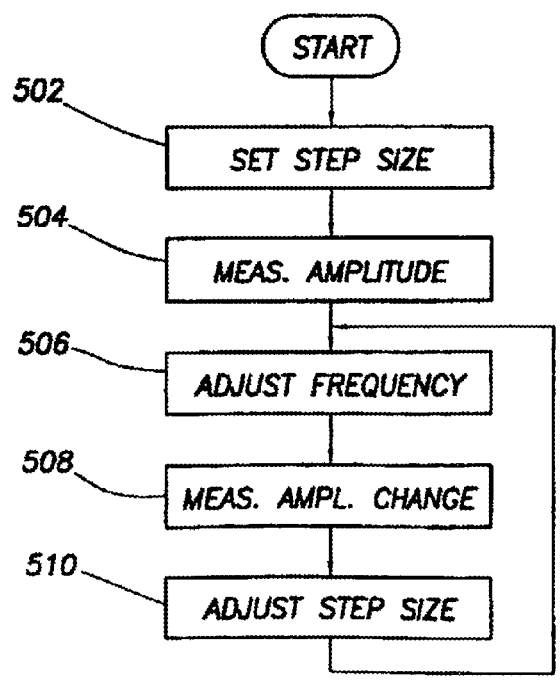
FIG. 6 shows a method for adaptive tracking of a resonance frequency.
Figure 7:
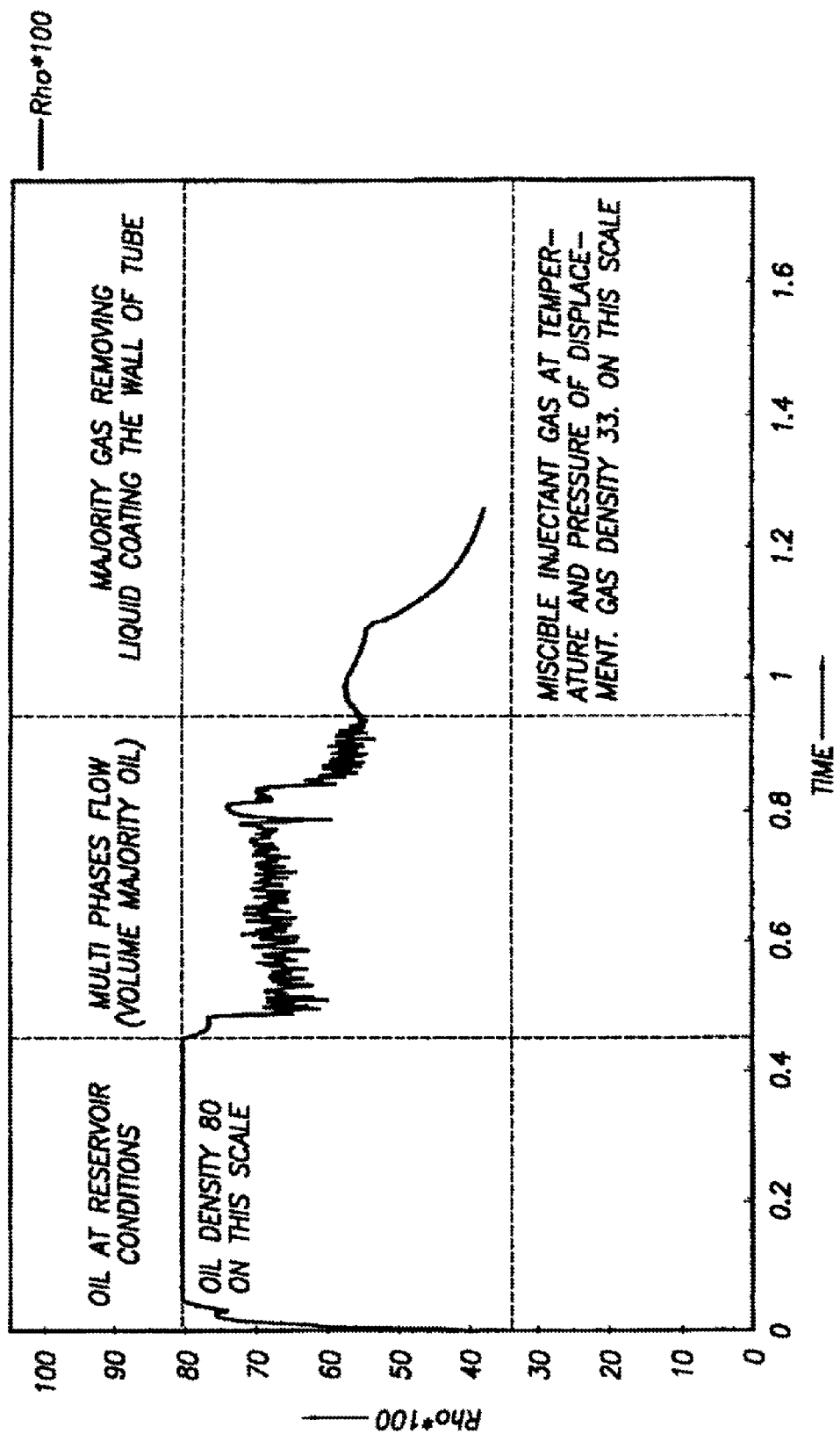
FIG. 7 shows a graph of a measured density as a function of time.

In a second method, the measurement module adaptively tracks the resonance frequency using a feedback control technique. One implementation of this method is shown in FIG. 6.

An initial step size for changing the frequency is chosen in block 502. This step size can be positive or negative, to respectively increase or decrease the frequency. In block 504, the vibration source is activated and an initial amplitude measurement is made. In block 506, the vibration frequency is adjusted by an amount determined by the step size. In block 508, a measurement of the amplitude at the new frequency is made, and from this, an estimate of the derivative can be made. The derivative may be estimated to be the change in amplitude divided by the change in frequency, but the estimate preferably includes some filtering to reduce the effect of measurement noise. From this estimated derivative, a distance and direction to the resonance peak can be estimated. For example, if the derivative is large and positive, then referring to FIG. 5 it becomes clear that the current frequency is less than the resonance frequency, but the resonance frequency is nearby. For small derivatives, if the sign of the derivative is changing regularly, then the current frequency is very near the resonance frequency. For small negative derivatives without any changes of sign between iterations, the current frequency is much higher than the resonance frequency. Returning to FIG. 6, this information is used to adjust the step size in block 510, and the digital signal processor 402 returns to block 506. This method may work best for providing a fast measurement response to changing fluid densities.

Figure 8:
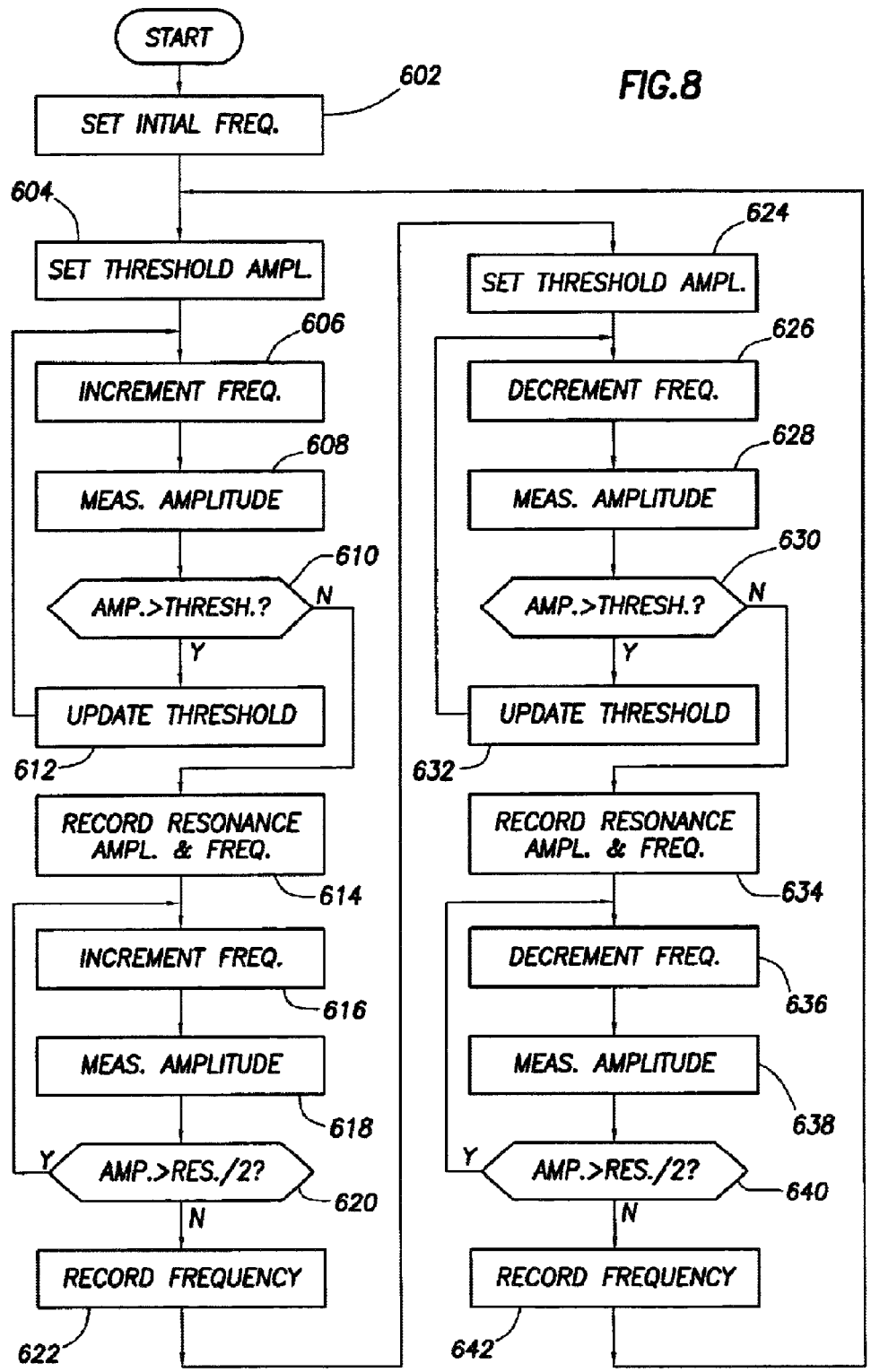
FIG. 8 shows a method for measuring resonance peak frequency, amplitude, and width.

In a third method, the measurement module employs an iterative technique to search for the maximum amplitude as the frequency is discretely varied. Any of the well-known search algorithms for minima or maxima may be used. One illustrative example is now described, but it is recognized that the invention is not limited to the described details. In essence, the exemplary search method uses a back-and-forth search method in which the measurement module sweeps the vibration source frequency from one half-amplitude point across the peak to the other half-amplitude point and back again. One implementation of this method is shown in FIG. 8. In block 602, vibration is induced at an initial (minimum) frequency. In block 604, the vibration amplitude at the current vibration frequency is measured and set as a threshold. In block 606, the frequency is increased by a predetermined amount, and in block 608, the amplitude at the new frequency is measured. Block 610 compares the measured amplitude to the threshold, and if the amplitude is larger, then the threshold is set equal to the measured amplitude in block 612. Blocks 606-612 are repeated until the measured amplitude falls below the threshold. At this point, the threshold indicates the maximum measured amplitude, which occurred at the resonance peak. The amplitude and frequency are recorded in block 614. The frequency increases and amplitude measurements continue in blocks 616 and 618, and block 620 compares the amplitude measurements to half the recorded resonance frequency. Blocks 616-620 are repeated until the amplitude measurement falls below half the resonance peak amplitude, at which point, the half-amplitude frequency is recorded in block 622. Blocks 624-642 duplicate the operations of corresponding blocks 602-622, except that the frequency sweep across the resonance peak occurs in the opposite direction. For each peak crossing, the measurement module records the resonance amplitude and frequency, and then records the subsequent half-amplitude frequency. From this information the peak width and asymmetry can be determined, and the fluid density, viscosity, and multiple phase information can be calculated.

Deterministically Ascertained Model

A new technique for computing fluid density relies on a deterministically ascertained model of the vibrating tube densitometer. In physics terms, the vibrating tube densitometer is a boundary value problem for a mass loaded tube with both ends fixed. The problem of a simple tube with fixed ends is described well by the classical Euler-Bernoulli theory. However, the physics of the actual densitometer device is more complicated. In one embodiment of a model of the vibrating-tube densitometer shown in FIG. 1, 2, or 3, the following effects/factors are taken into consideration:

1. Effect of any tensile/compressive load caused by the housing on vibration of the tube;
2. Effect of the two magnets and saddles, their masses and their locations on the tube and their influence on the frequency;
3. Effect of pressure on tubing inside diameter ("ID"), outside diameter ("OD") and area moment of inertia;
4. Poisson's ratio of the tube material and its temperature dependence;
5. Poisson's effect due to internal pressure and the resulting change in the tension;
6. Effect of tension in the tube on the housing, which in turn changes the tension in the tube and vice versa;
7. Effect of thermal stress due to the existence of temperature gradient between the tube and housing;
8. Precise value of the elastic modulus of the material from which the rigid housing 102, bulkheads 104, and the flow tube 108 are made (e.g., the alloy Ti-6Al-4V);
9. Temperature dependence of the elastic modulus;
10. Effect of temperature on the values of water and air density used in calibration tests;
11. Effect of fluid flow on frequency;
12. Effect of Coriolis force on frequency; and
13. Effect of fluid viscosity on the resonant frequency of the tube.

For someone skilled in the art of the dynamics of vibration system, it can be shown that the basic equation describing the motion of simple vibrating tube in the densitometer is the Euler-Bernoulli theory $$EI\frac{\partial^4 \psi(x,t)}{\partial x^4} + \rho A \frac{\partial^2 \psi(x,t)}{\partial t^2} = 0$$

where
x=variable representing the distance from one end of the tube
t=time variable
Ψ=variable representing the transverse displacement of the tube
E=Young's modulus of the tube material
I=area moment of inertia
ρ=density of the tube
A=cross sectional area of the tube However, in reality, the actual densitometer is more complicated than a simple vibrating tube. The above equation must be modified in order to fully describe the motion of the densitometer. In one embodiment, a series of additional loading terms are added to the basic equation. Starting with Newton's law, in one embodiment, the total force acting on a small tube and fluid element of the tube is:

$$(m_T + m_L)\frac{\partial^2 \psi}{\partial t^2} = -EI\frac{\partial^4 \psi}{\partial x^4} + f_P + f_T + f_C + f_V + f_M \tag{1}$$

where
$m_L$=linear density of the fluid inside the tube
$m_T$=linear density of the tube material $f_P$=force on tube due to pressure
$f_T$=additional tensile force on tube
$f_C$=Coriolis force
$f_V$=force on tube due to fluid flow
$f_M$=additional mass loading due to the presence of the magnets From detailed force analysis, it can be shown that the forces are given by:

$$f_P = -PA\frac{\partial^2 \psi}{\partial x^2}$$

$$f_T = T\frac{\partial^2 \psi}{\partial x^2}$$

$$f_C = -2m_L V\frac{\partial^2 \psi}{\partial t \partial x}$$

$$f_V = -m_L V^2 \frac{\partial^2 \psi}{\partial t \partial x}$$

$$f_M = M_1 \frac{\partial^2 \psi}{\partial t^2}\delta(x-x_1) + M_2 \frac{\partial^2 \psi}{\partial t^2}\delta(x-x_2)$$

where
T=tension in the tube
V=flow velocity of the fluid
$M_{1,2}$=masses of the two magnets on the tube
$X_{1,2}$=locations of the two magnets on the tube
$\delta(x-x_{1,2})$=Dirac delta-functions at $x_1$ and $x_2$ In the above differential equation, T is the total tension on the tube. Because of Poisson effect, since the vibrating tube is fixed at two ends by its housing, the presence of pressure inside the tube produces additional tension on the tube which can be found to be, assuming a perfectly rigid housing $$T_P = \frac{\pi}{2}vb^2 P$$

where $v$ is the Poisson's ratio of the tube material and b is the inner radius of the tube. However, because the housing does not have infinite rigidity, the tension from the tube will result in tension on the housing, which in turn will lead to slightly reduce tension in the tube. Analysis of this process leads to a modification of the expression for tension due to pressure:

$$T_P = \frac{\pi}{2}b^2 vP \cdot \left[\lim_{n\to\infty}\sum_{n=0}^{\infty}(-\eta)^n\right] = \frac{\pi b^2 vP}{2(1+\eta)}$$

where $\eta$ is a constant that is entirely determined by the geometry of the tube and the housing of the densitometer.

Furthermore, the existence of any temperature difference between the housing and the tube leads to a thermal stress in the tube which can be found to be:

$$F_t = \frac{\pi \alpha E}{4}(a^2 - b^2)(T_h - T_t)$$

where $\alpha$ is the thermal expansion coefficient of the tube material, $T_h$ and $T_t$ are the temperature of the housing and the tube, a, b are the outer and inner diameter of the tube, respectively.

The 4th order partial differential equation (1) with fixed ends boundary conditions can be solved analytically using well-established techniques such as the method of Laplace transform. The solution yields a complex frequency equation consisting of various combination of transcendental functions of the form $$2\varepsilon_1^7 \varepsilon_2^3 \cos(\varepsilon_1) + 4\varepsilon_1^5 \varepsilon_2^5 \cos(\varepsilon_1) + 2\varepsilon_1^3 \varepsilon_2^7 \cos(\varepsilon_1) - 2\varepsilon_1^7 \varepsilon_2^3 \cosh(\varepsilon_2) - \quad (2)$$
$$4\varepsilon_1^5 \varepsilon_2^5 \cosh(\varepsilon_2) + \ldots + (\beta L)^8 \alpha_1 \alpha_2 \varepsilon_1^3 \varepsilon_2 \cos(\varepsilon_1)\sinh(\varepsilon_2)\sinh(\varepsilon_2 \xi_1)$$
$$\sinh[\varepsilon_2(\xi_2 - \xi_1)]\sinh[\varepsilon_2(1-\xi_2)] + (\beta L)^8 \alpha_2 \varepsilon_1^3 \varepsilon_2 \cosh(\varepsilon_2)$$
$$\sinh(\varepsilon_2)\sinh(\varepsilon_2 \xi_1)\sinh[\varepsilon_2(\xi_2 - \xi_1)]\sinh[\varepsilon_2(1-\xi_2)] = 0$$

where $$\xi_{1,2} = \frac{x_{1,2}}{L},$$

$$\alpha_{1,2} = \frac{M_{1,2}}{(m_t + m_f)\cdot L},$$

$$\varepsilon_1 = L\sqrt{\frac{B}{2} + \frac{1}{2}\sqrt{B^2 + 4\beta^2}},$$

$$\varepsilon_2 = L\sqrt{-\frac{B}{2} + \frac{1}{2}\sqrt{B^2 + 4\beta^2}},$$

$$B = \frac{\pi}{4}\left[b^2(P)P\left(1 - \frac{2v}{1+\eta}\right) + \frac{\alpha E(T)}{1+\eta}[a^2(P) - b^2(P)](T_h - T_t)\right]$$

L=length of the vibrating tube

Note that for clarity, many terms in the frequency equation have been omitted. But one skilled in the art of partial differential equations can generate these terms.

Once temperature, pressure, and fluid density are known, Equation (2) can be solved to yield the wave number $\beta_0$ that is related to the resonance frequency $f_0$ of the vibrating tube as $$f_0 = \frac{\beta_0^2}{2\pi L^2}\sqrt{\frac{E(T_t)\cdot I(T_t)}{m_t + m_f}} \quad (3)$$

where
$f_0$ is the resonance frequency of the tube with fluid having density $\rho_f$ at pressure P and temperature $t_t$ and housing at temperature $t_h$.

$$m_t = \rho_t \cdot \frac{\pi}{4}[a^2(P) - b^2(P)]$$

the linear density of the tube, $$m_f = \rho_f \cdot \frac{\pi}{4}b^2(P)$$

the linear density of fluid,
$E(t_t)$ is the temperature dependent Young's modulus,
$I(t_t)$ temperature dependent area moment of inertia of the tube.
a(P), b(P) are the outer and inner diameter of the vibrating tube at pressure P.

$\beta_0$ is not a constant. Rather it depends on all the physical parameters of the densitometer. Thus, change in temperature, pressure, fluid density, mass of the magnets, Young's modulus values all leads to change in $\beta_0$.

Solving Equation (2) constitutes a forward problem: given $\rho_f$, P, $t_h$ and $t_t$, find the resonance frequency of the vibrating tube.

Figure 9:
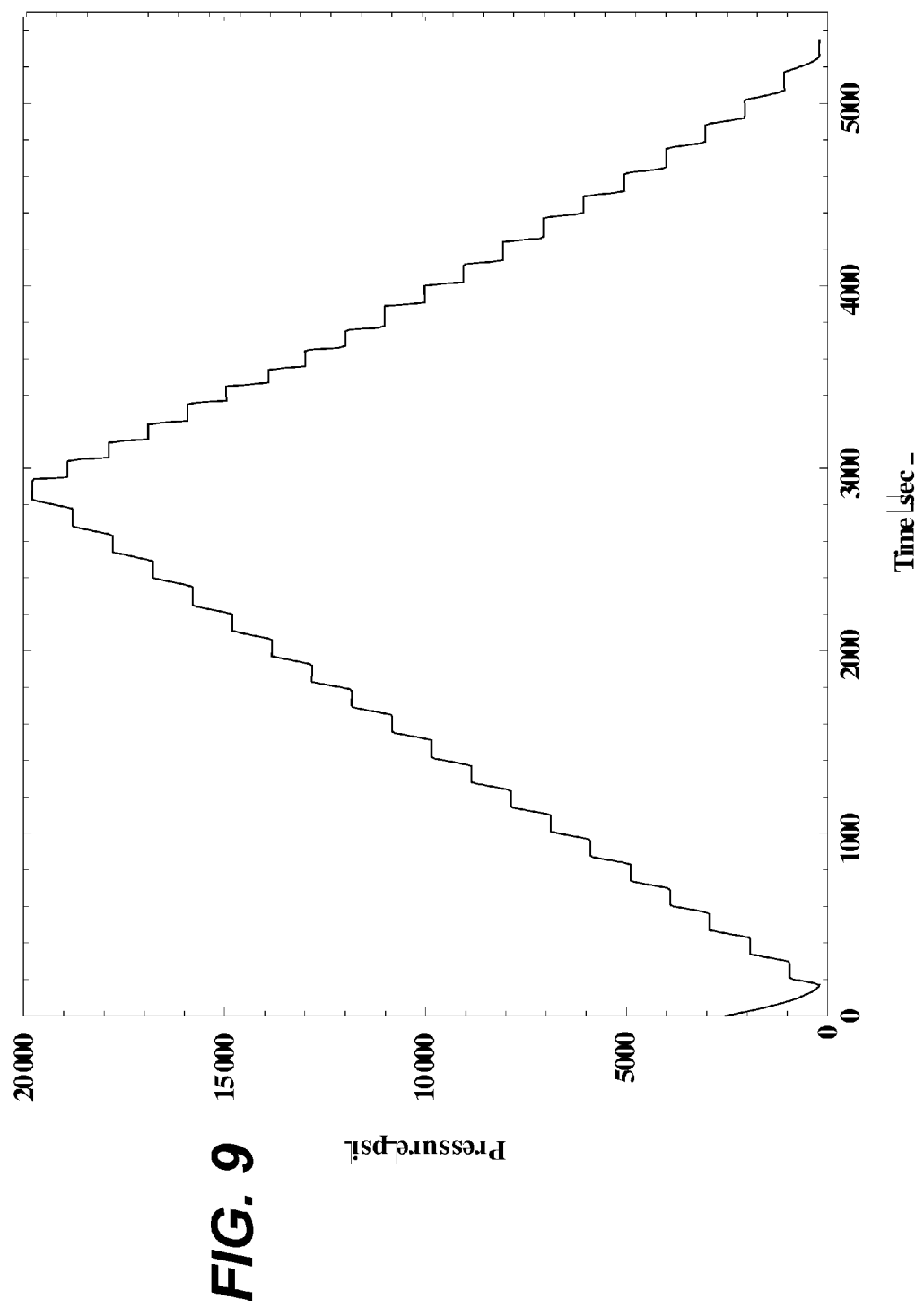
FIG. 9 shows a pressure-time profile used in assessing the accuracy of the fluid density measurement technique.
Figure 10:
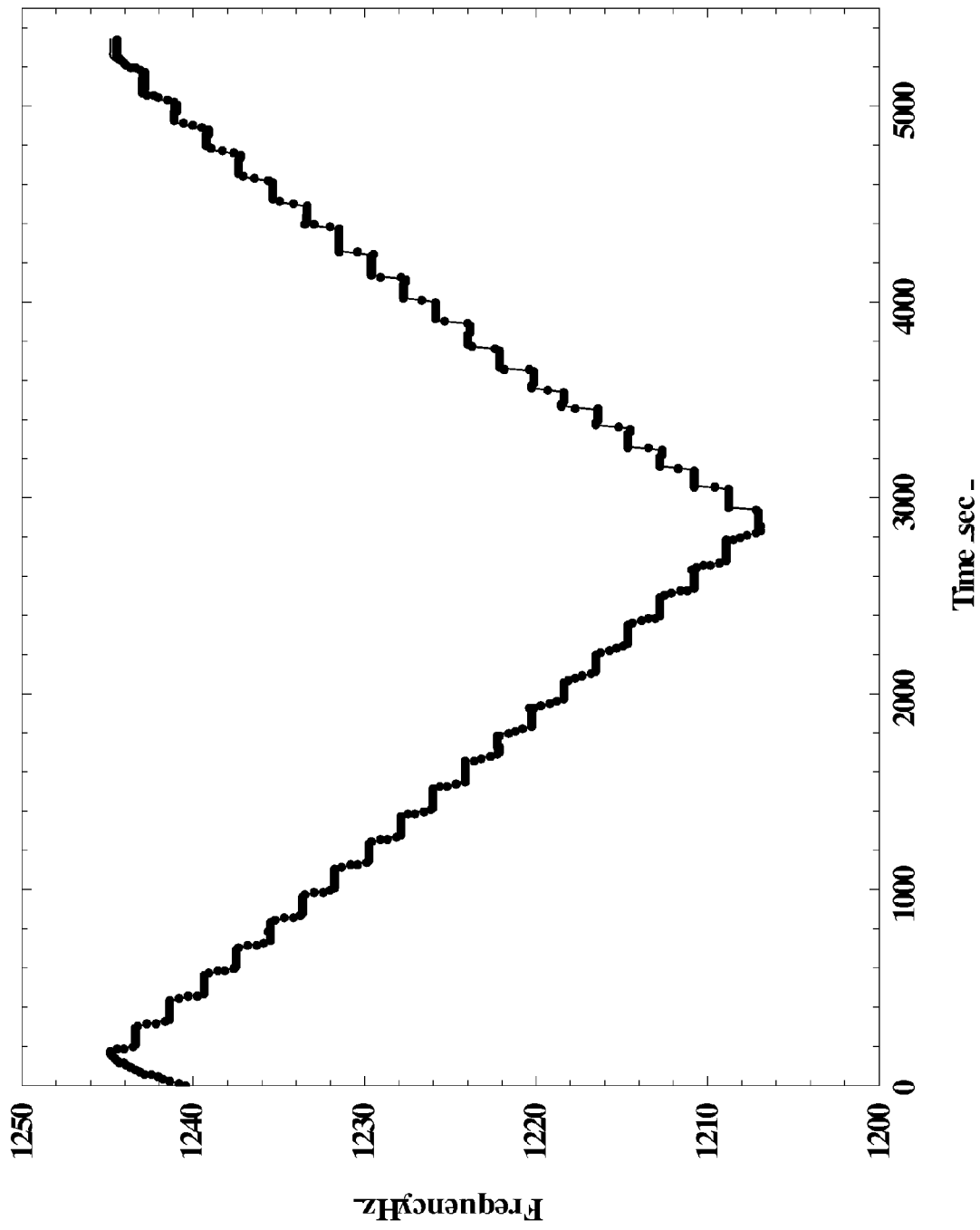
FIG. 10 shows the result of the assessment of the accuracy of the fluid density measurement technique.

The accuracy of the above solution is demonstrated in FIGS. 9 and 10 for a prototype densitometer operating at room temperature with water in the tube under pressure up to 20,000 psi FIG. 9 shows the pressure-time profile. FIG. 10 shows a line chart representing a forward model prediction of frequency versus time based on the pressure-time profile in FIG. 9 and dots representing measured values. As can be seen, the measured values correspond closely to the predicted curve.

In obtaining the result shown in FIG. 10, only a single adjustable parameter is necessary. Furthermore, this adjustable parameter can be easily fixed by comparing the theoretical frequency and measured frequency at a single pressure, temperature and fluid density point. In other words, a single point calibration is all that is necessary to match the complete pressure profile.

Figure 11:
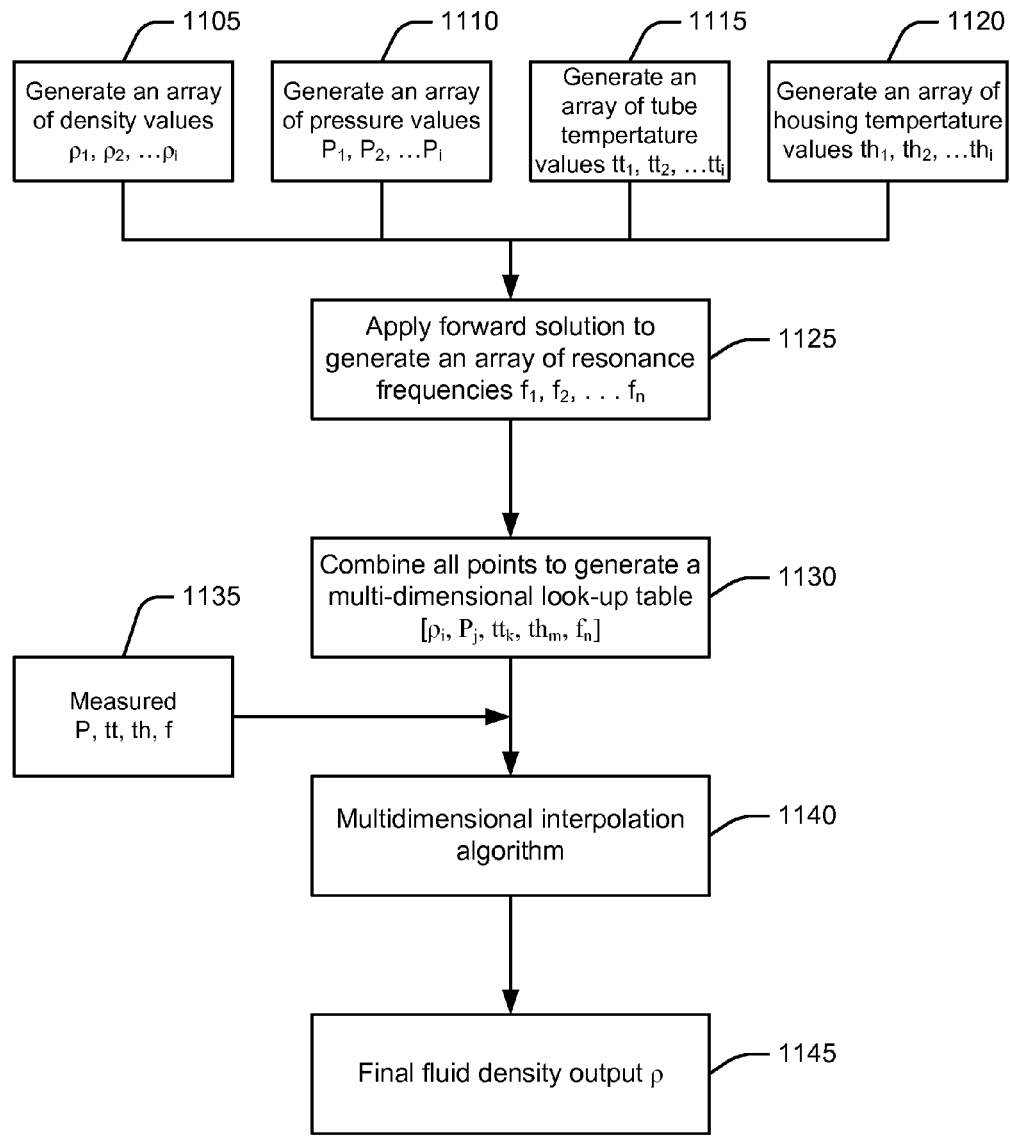
FIGS. 11 and 12 are flow charts.

With solution of the forward problem, the inverse problem of given the measured resonance frequency $f_0$, P, $T_t$ and $T_h$, find the density $\rho_f$ of the fluid in tube, becomes possible. For example, as shown in FIG. 11, a technique for solving the inverse problem includes generating an array of density values $\rho_1, \rho_2 \ldots \rho_i$ (block 1105), an array of pressure values $P_1, P_2, \ldots P_i$ (block 1110), an array of tube temperature values $tt_1, tt_2, \ldots tt_i$ (block 1115), and an array of housing temperature values $th_1, th_2, \ldots th_i$ (block 1120). The forward solution is then applied to a set of n values of $\rho$, P, $T_t$ and $T_h$, to generate a list of corresponding resonance frequencies $f_1, f_2, \ldots f_n$ at these combinations of measured quantities (block 1125). A look-up table is then generated from the corresponding values of $\rho$, P, $T_t$, $T_h$, and f (block 1130) The look-up table can be stored either in the sensor's electronic memory or stored in a computer. During operation of the densitometer, each measured set of data points ($\rho$, P, $t_t$, $t_h$) is checked against the look-up table (block 1135). A computer algorithm (such as a multidimensional interpolation algorithm) (block 1140) is used to identify the density of the fluid (block 1145).

Figure 12:
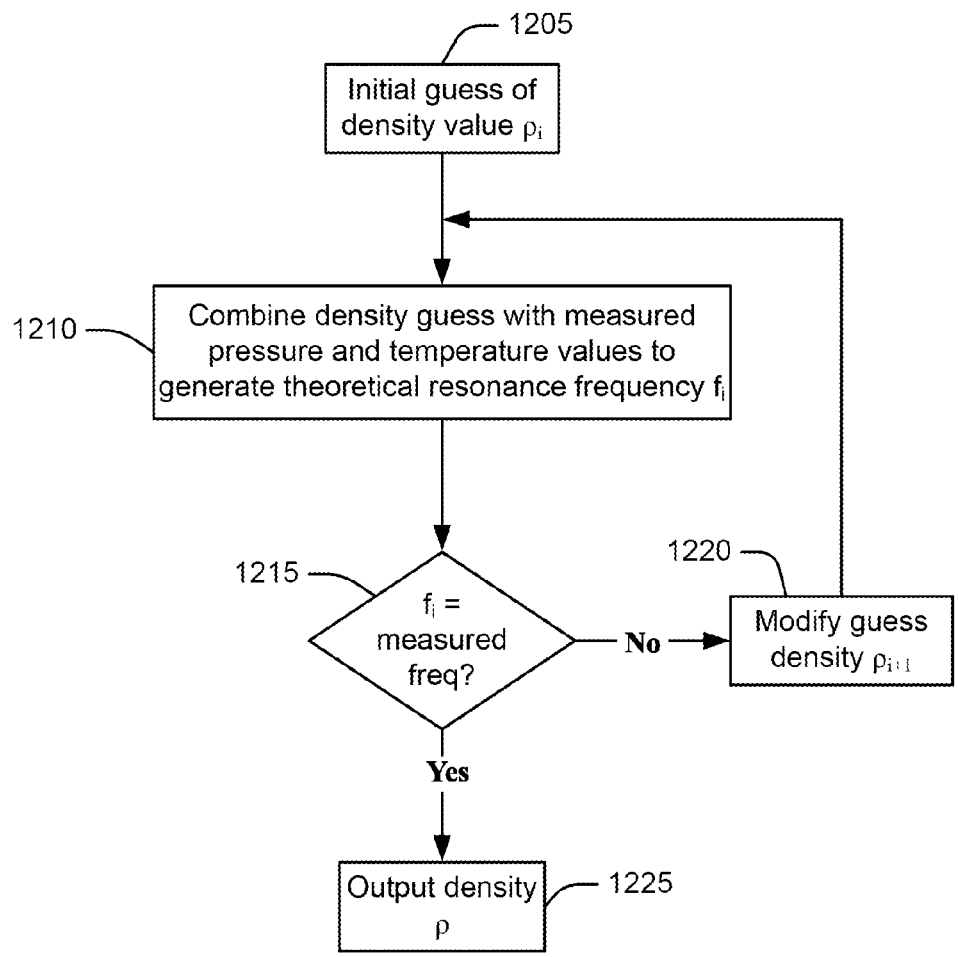

In another embodiment a trial-and-error method of finding the density of fluid, illustrated in FIG. 12, is used. In this technique, an initial guess of density value $\rho_i$ is made (block 1205). That guessed density value is then combined with measured pressure and temperature values to generate a theoretical resonance frequency $f_i$ (block 1210). The theoretical resonance frequency is then compared to the measured frequency (block 1215). If they are not substantially the same (i.e., within 0.1 percent), the density guess is modified to generate a new density guess $\rho_{i+1}$ (block 1220) and blocks 1210 and 1215 are repeated. These blocks are repeated until the theoretical resonance frequency is substantially the same as the measured frequency. At that point, the density $\rho$ is output (block 1225).

Numerical Solution

In another embodiment, the $4^{th}$ order partial differential equation (1) with known boundary conditions is solved numerically, using well established numerical methods such as Runge-Kutta method, finite difference method, finite element method, shooting method, etc.

One example using the shooting method is explained below. The densitometer with both ends fixed presents a classic eigenvalue problem in mathematics. For simplicity of discussion, one can neglect the effect of all external forces listed above. After separation of variables, the eigenvalue problem can then be written as $$\frac{d^4 \psi(x)}{dx^4} - \beta^4 \psi(x) = 0,$$

$$\psi(0) = \psi(1) = 0, \psi'(0) = \psi'(1) = 0.$$

Figure 13:
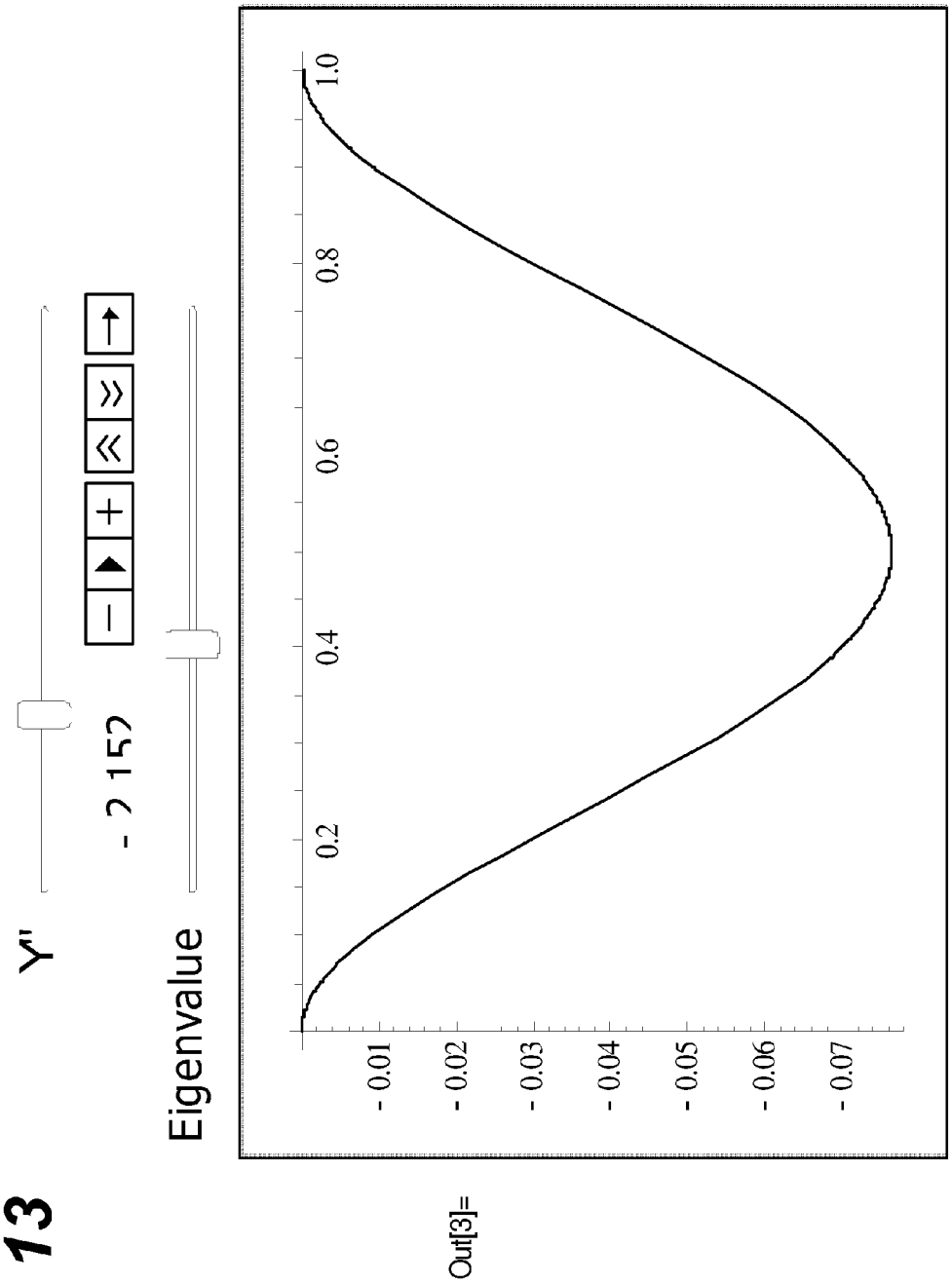
FIG. 13 illustrates a numerical solution.

The two point boundary value problem can be cast into an initial value problem using the shooting method:

$$\frac{d^4 \psi(x)}{dx^4} - \beta^4 \psi(x) = 0,$$

$$\psi(0) = \psi'(0) = 0, \psi''(0) = \alpha, \psi'''(1) = const.$$

where the value of $\alpha$ and eigenvalue $\beta$ are to be determined by matching the boundary condition at the other end of the tube: $\psi(1)=0$, $\psi'(1)=0$. This is illustrated in FIG. 13 where the Mathematica software is used to vary $\psi'''(0)$ and $\beta$ until the conditions $\psi(1)=0$, $\psi'(1)=0$ are met. At this point, the shape of the curve identifies the first eigenmode. Its eigenvalue determines the fundamental frequency.

In one embodiment, this process is automated.

Once the eigenvalue is found, in one embodiment, the corresponding frequency is then calculated. At this stage, the process described above becomes applicable.

Determination of Young's Modulus

Equation (3) above uses the temperature dependent Young's modulus of the tube ($E(t_t)$). Techniques for determining $E(t_t)$ are now described.

Determination of Young's Modulus at Room Temperature

Speed of Sound Using Accelerometers to Measure Time of Flight

For an isotropic material, its speed of sound is determined by Young's modulus E and density $\rho$ as $$c = \sqrt{\frac{E}{\rho}}.$$

Using compressional wave, previously this relationship was used to roughly estimate E at room temperature using accelerometers to measure time of flight two points. However, this method has flaws. One flaw is that the time resolution is insufficient given the short (~6 inches) separation between the two accelerometers. But more importantly, both the compressional AND shear wave velocity needed to be considered in order to arrive at a better estimate of the E value:

$$E = V_s^2 \rho \frac{3V_c^2 - 4V_s^2}{V_c^2 - V_s^2}.$$

With the short separation and small shear wave signal, using accelerometers to detect both compressional and shear wave is a challenge.

Ultrasonic Pulse-Echo Method

An alternative way to determine speed of sound is using ultrasonic transceivers. With the standard pulse echo method, a high frequency (5 MHz) ultrasonic pulse is transmitted into the tube and the echo detected. With known length of the tube and measured time of flight, formula (2) may be used. Compared to the method of using accelerometer, the ultrasonic method has better time resolution and thus gives more accurate E values. Unfortunately, shear wave again posed a serious challenge. Furthermore, the thin wall thickness is comparable to the wave length. This will lead to complex modes of wave propagation in the tube thus render equation (3) inaccurate.

Beam Bending for Bulk Young's Modulus Determination

Figure 14:
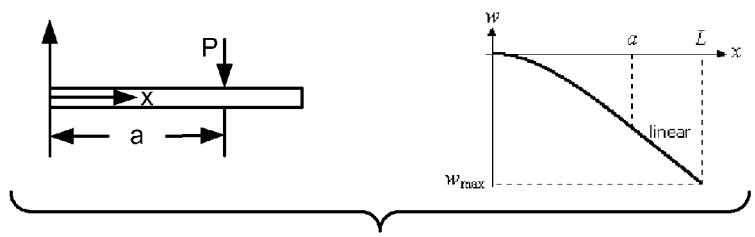
FIG. 14 illustrates the deflection of a cantilever hanging under its own weight.
Figure 15:
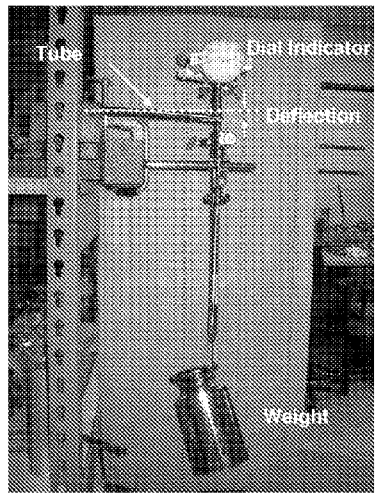
FIG. 15 shows a test rig.
Figure 16:
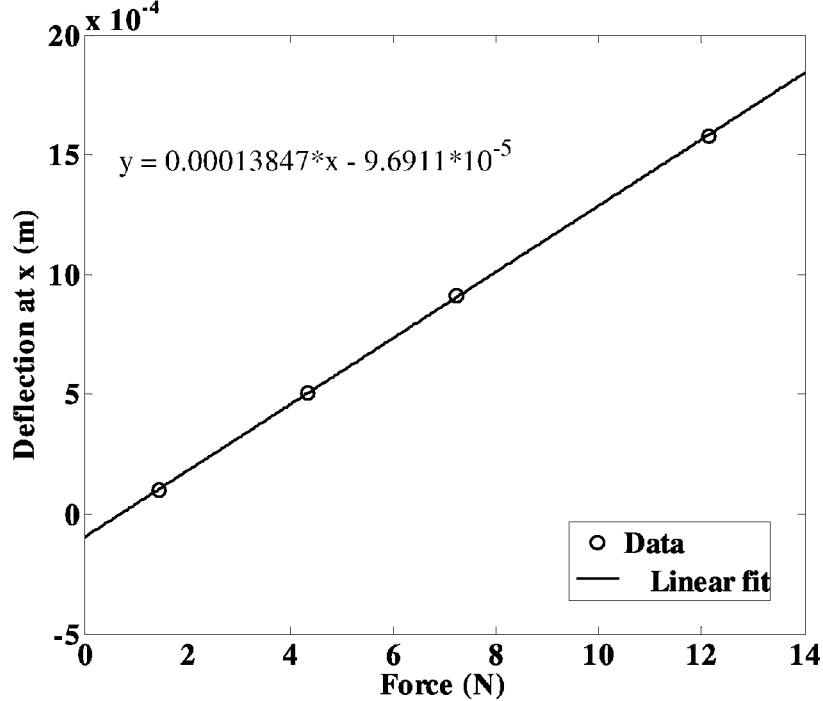
FIG. 16 illustrates the measured deflection of the cantilever illustrated in FIG. 15.

From Euler's beam theory, the deflection of a cantilever 1405 hanging under its own weight (see FIG. 14), is described by:

$$w(x) = \begin{cases} -\dfrac{Px^2}{6EI}(3a-x) & 0 \le x \le a \\ -\dfrac{Pa^2}{6EI}(3x-a) & a \le x \le L \end{cases}$$

where P is the weight at position a, E is Young's modulus, I is the area moment of inertia of the tube which can be calculated knowing the outside diameter and inside diameter of the tube. The inventor set up a simple experiment, shown in FIG. 15, using known weights and a known tube length of the tube. A dial indicator with resolution of 0.01 mm was used to measure the defection of the tube under varying weights. The measured deflection as a function of changing weights (in Newtons) is shown in FIG. 16. The measured data is shown as open circles and is very close to linear. The reciprocal of the slope of a line fit to the measured data, as shown on FIG. 16, gives Young's modulus at room temperature.

Using the ultrasonic method and the beam bending method, the Young's modulus value of several tubes at room temperature was determined. The results are listed in Table 2 below.

TABLE 2

Measured Young's modulus values at room temperature.

| Method | 7.5" tube | 10" tube | 13" tube |
|---|---|---|---|
| Ultrasonic pulse-echo | 76.2 GPa | 79.3 GPa | 73.4 GPa |
| Beam bending | 73 GPa | 80.7 GPa | 73.5 GPa |

Note that the measured Young's modulus values are below the 90-120 GPa that is generally quoted in the literature.

Determination of Young's Modulus at Elevated Temperature

Theoretical Derivation of the Method

The methods listed in the previous section work reasonably well at room temperature. But attempt to extend them to higher temperatures is challenging. Not only the sensors have limited temperature range, setting up the measurement inside an oven is also problematic.

The vibrating densitometer itself can be used to determine Young's modulus at elevated temperatures, provided the response of the densitometer to fluid of known density at elevated temperatures can be measured accurately. This approach is described in detail in the following.

The measured resonance frequency of the vibrating tube is expressed as $$f_0 = \frac{\beta_0^2(E(T_t), T_h, T_t, P, m_f)}{2\pi L^2} \sqrt{\frac{E(T_t) \cdot I}{m_t + m_f}} \qquad (4)$$

where $\beta_0$=Root of the complicated frequency equation (i.e., equation (2)),
$T_h$=Temperature of densitometer housing,
$T_t$=Temperature of vibrating tube,
P=Fluid pressure,
$m_t$=Linear density of the tube,
$m_f$=Linear density of the fluid,
I=Area moment of inertia of the tube,
L=Length of tube,
$E(T_t)$=Young's modulus as function of tube temperature.

It can be shown that the root k depends only weakly on $E(T_t)$ thus for all practical purposes can be treated as being independent of temperature. If one assumes a temperature independent Young's modulus value of $E_0$, then equation (4) can be used to calculate a "theoretical" frequency $f_0(T_t)$ as:

$$f_0(T_t) = \frac{\beta_0^2(E_0, T_h, T_t, P, m_f)}{2\pi L^2} \sqrt{\frac{E_0 \cdot I}{m_t + m_f}}. \qquad (5)$$

Without loss of generality, one can express the temperature dependent Young's modulus in Equation (4) in the form of a Taylor series as:

$$E(T_t) = E_0(1 + aT_t + bT_t^2 + cT_t^3 + \dots), \qquad (6)$$

Substituting Equation (6) into Equation (4), taking the ratio of the squares of Equations (4) and (5), one arrives at the following relation:

$$E(T_t) = E_0 \frac{f^2}{f_0^2}. \qquad (7)$$

Note that in deriving equation (7), the assumption that β is only a slow-varying function of E(T) is used. That is, it is assumed that $\beta_0(E_0, T_h, T_t, P, m_f) \approx \beta_0(E(T_t), T_h, T_t, P, m_f)$. Based on this relationship, one can obtain the temperature dependent Young's modulus by taking the ratio of the square of measured frequency to the square of the theoretically calculated frequency with an assumed constant Young's modulus.

Experimental Proof of the New Method

Figure 17:
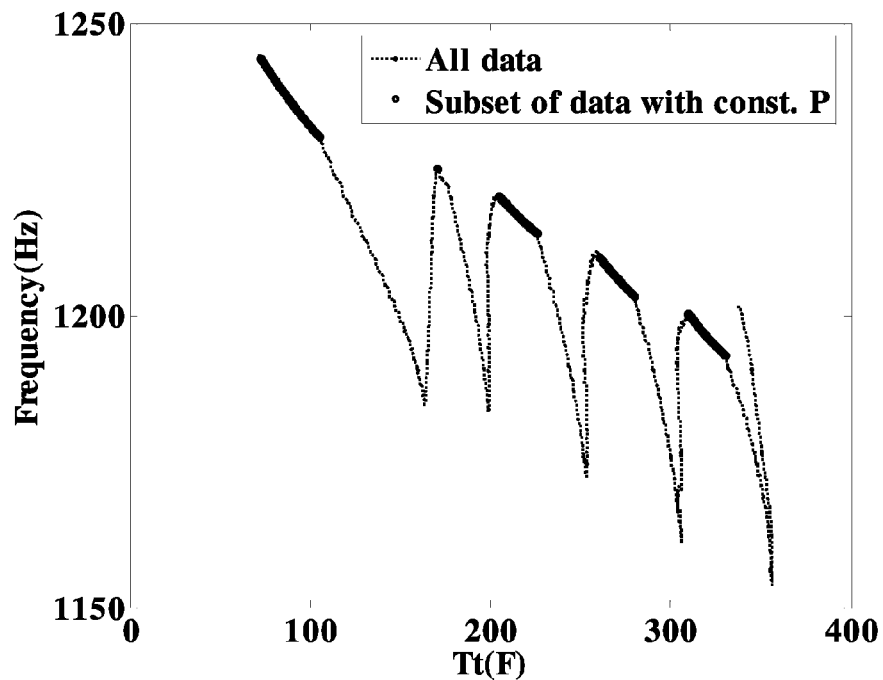
FIG. 17 shows experimental data.

The inventor checked this assertion against experimental data obtained for an existing sensor. In FIG. 17, the data is plotted against measured tube temperature. The solid portions of the plot indicate the subset of the data with constant fluid pressure values around 400 psi.

This subset of data is chosen to concentrate on the temperature behavior of the sensor alone without interference from the pressure behavior.

Using a constant Young's modulus value of $E_0$=93.9 GPa, a theoretical frequency response of the sensor $f_0(E_0, T_h, T_t, P, m_f)$ was calculated using the experimentally measured housing temperature and tube temperature, as well as measured pressure, and known density of water at such temperature and pressure. The ratio of the square of the theoretical $f_0$ and measured f for the subset of data is plotted against measured tube temperature as shown in FIG. 18.

Using a constant Young's modulus value of $E_0$=93.9 GPa, a theoretical frequency response of the sensor $f_0(E_0, T_h, T_t, P, m_f)$ was then calculated using the experimentally measured housing temperature and tube temperature, as well as measured pressure, and known density of water at such temperature and pressure. The ratio of the square of the theoretical $f_0$ and measured f for the subset of data was plotted against measured tube temperature as shown in FIG. 18.

Figure 18:
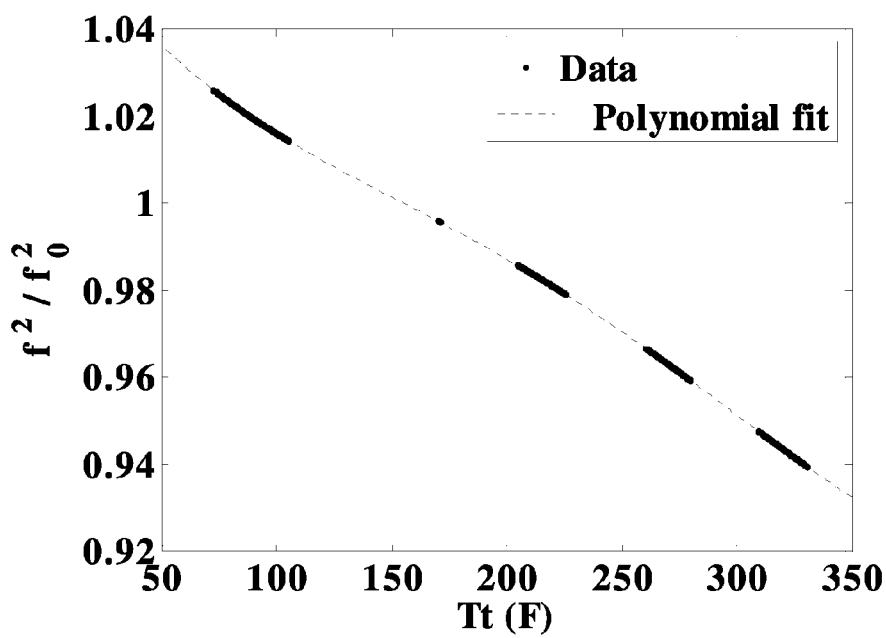
FIGS. 18 and 19 show analysis of the experimental data.
Figure 19:
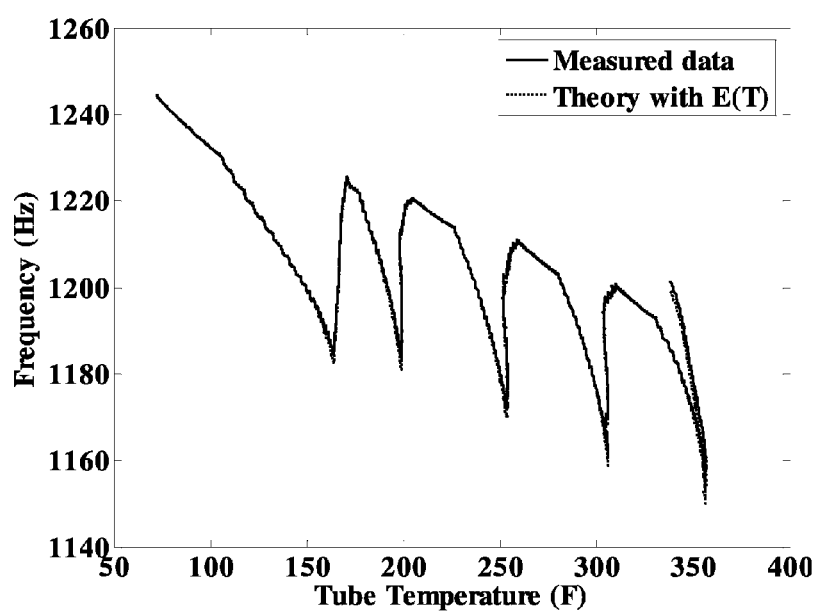

From FIG. 18, the 4th order polynomial fit to the data yields the desired temperature dependence of Young's modulus of the tube at elevated the temperatures. This relation is then substituted back into the theoretical frequency equation to produce the final theoretical prediction of resonance frequency. This final result is shown in FIG. 19.

With the exception at around 350 F, the residual using the new method lies within ±1 Hz. Furthermore, this technique is self-calibrated in that there is no calibration constant in the final theory. It should also be noted that none of the temperature sensors have been calibrated, which may lead to some additional experimental errors.

Technique for Solving the Frequency Equation (Equation 2)

Figure 20:
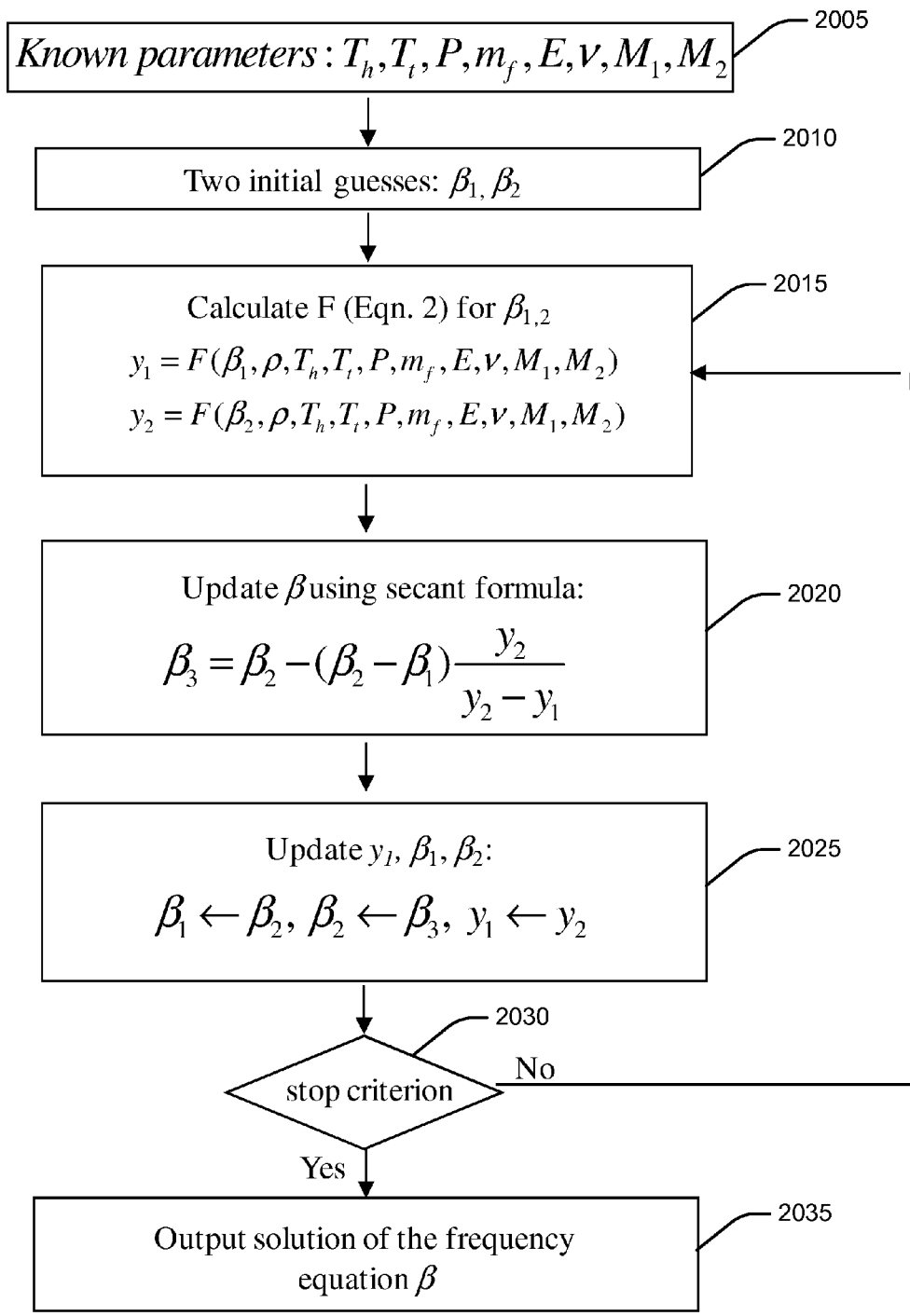
FIG. 20 shows an embodiment of a technique for solving the frequency equation.

An embodiment of a technique for solving the frequency equation (equation (2)), illustrated in FIG. 20, begins with known parameters $T_h$, $T_f$, P, $m_f$, E, v, $M_1$, and $M_2$ (block 2005). The technique makes two initial guesses at $\beta_0$: $\beta_1$ and $\beta_2$ (block 2010). The technique then calculates F for $\beta_1$ and $\beta_2$ using equation (2) (block 2015). $\beta_3$, an updated $\beta$, is then calculated from $\beta_1$ and $\beta_2$ using the secant formula (block 2020). The values of $y_1$, $\beta_1$ and $\beta_2$ are then updated (block 2025). If a stop criterion has been reached (e.g., $\beta_1$-$\beta_2$<a threshold) (block 2030), the "Yes" branch from block 2030 is followed and the solution is output (block 2035). Otherwise, the technique returns to block 2015 ("No" branch from block 2030).

Figure 21:
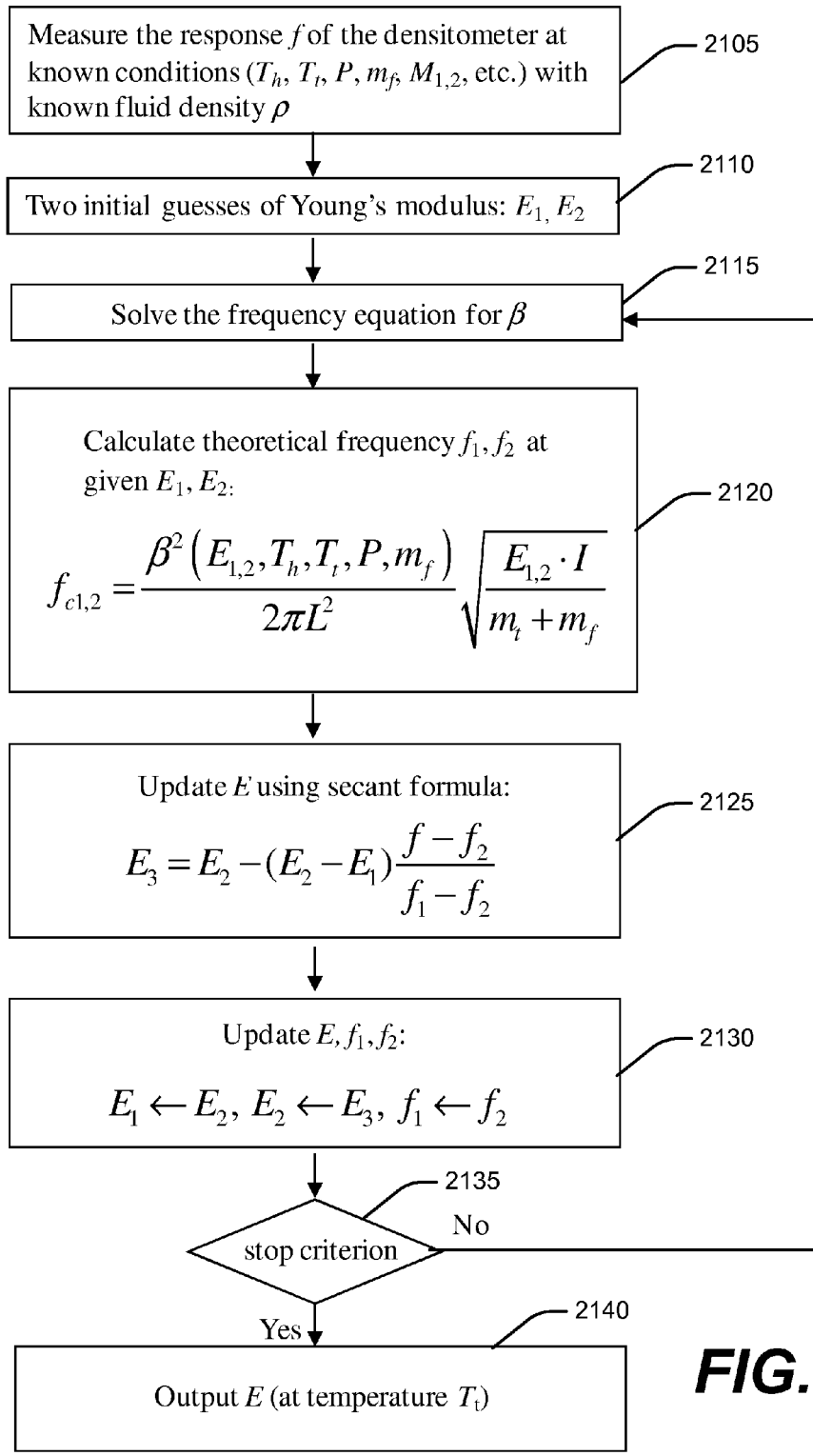
FIGS. 21-23 show techniques for obtaining the temperature dependent Young's modulus.

Technique to Obtain the Temperature Dependent Young's Modulus Based on Calibration Measurement An embodiment of a technique to obtain the temperature dependent Young's Modulus based on calibration measurements, illustrated in FIG. 21, begins by measuring the response f of the densitometer at known conditions ($T_h$, $T_f$, P, $m_f$, E, v, $M_1$, and $M_2$, etc.) with known fluid density $\rho$ (block 2105). The technique then makes two initial guesses of Young's modulus: $E_1$ and $E_2$ (block 2110). The technique then solves the frequency equation (equation (2)) for $\beta$ (block 2115). The technique then calculates the theoretical frequencies f1 and f2 at E1 and E2 using the equation shown in the figure (block 2120). The technique then updates E using the secant formula (block 2125) and updates E, $f_1$, and $f_2$ (block 2130). If a stop criterion has been reached (e.g., $E_1$-$E_2$<a threshold), the "Yes" branch from block 2135 is followed and a solution is output (block 2140). Otherwise, the technique returns to block 2115 ("No" branch from block 2135). The solution returned at block 2140 is at temperature $T_f$.

Figure 22:
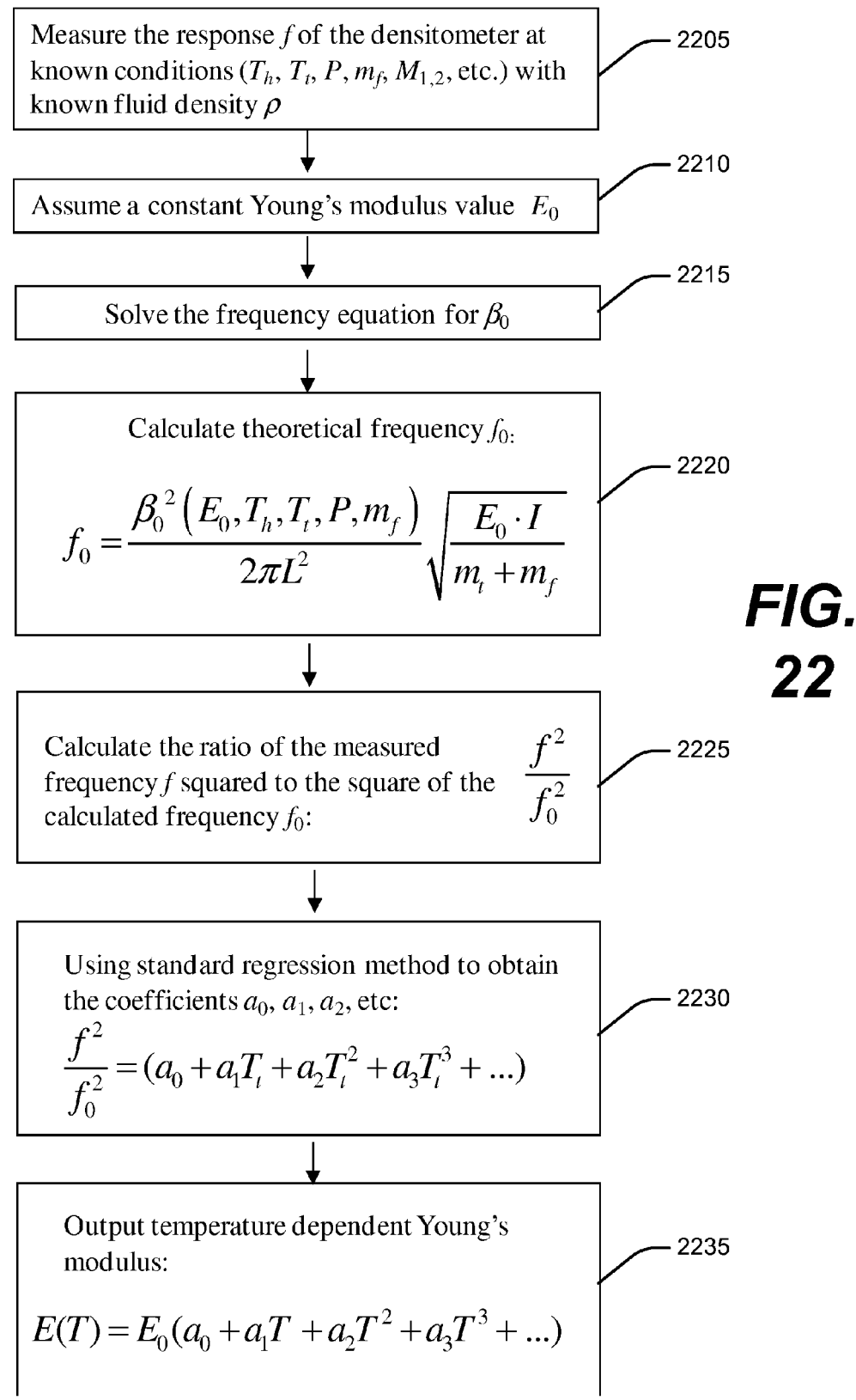

Alternative Technique to Obtain the Temperature Dependent Young's Modulus Based on Calibration Measurement An alternative embodiment of a technique to obtain the temperature dependent Young's Modulus based on a calibration measurement, illustrated in FIG. 22, begins by measuring the response f of the densitometer at known conditions ($T_h$, $T_f$, P, $m_f$, E, v, $M_1$, and $M_2$, etc.) with a known fluid density $\rho$ (block 2205). The technique next assumes a constant Young's modulus value $E_0$ (block 2210). The technique next solves the frequency equation (equation (2)) for $\beta_0$ (block 2215). The technique next calculates the theoretical frequency $f_0$ using the equation shown in the figure (block 2220). The technique next calculates the ratio of the square of the measured frequency $f^2$ to the square of the calculated frequency $f_0^2$ (block 2225). The technique next uses a standard regression method to obtain the coefficients $a_0$, $a_1$, $a_2$, etc. to the equation shown in the figure (block 2230). The technique then outputs the temperature dependent Young's modulus calculated using the equation shown in the figure (block 2235).

Figure 23:
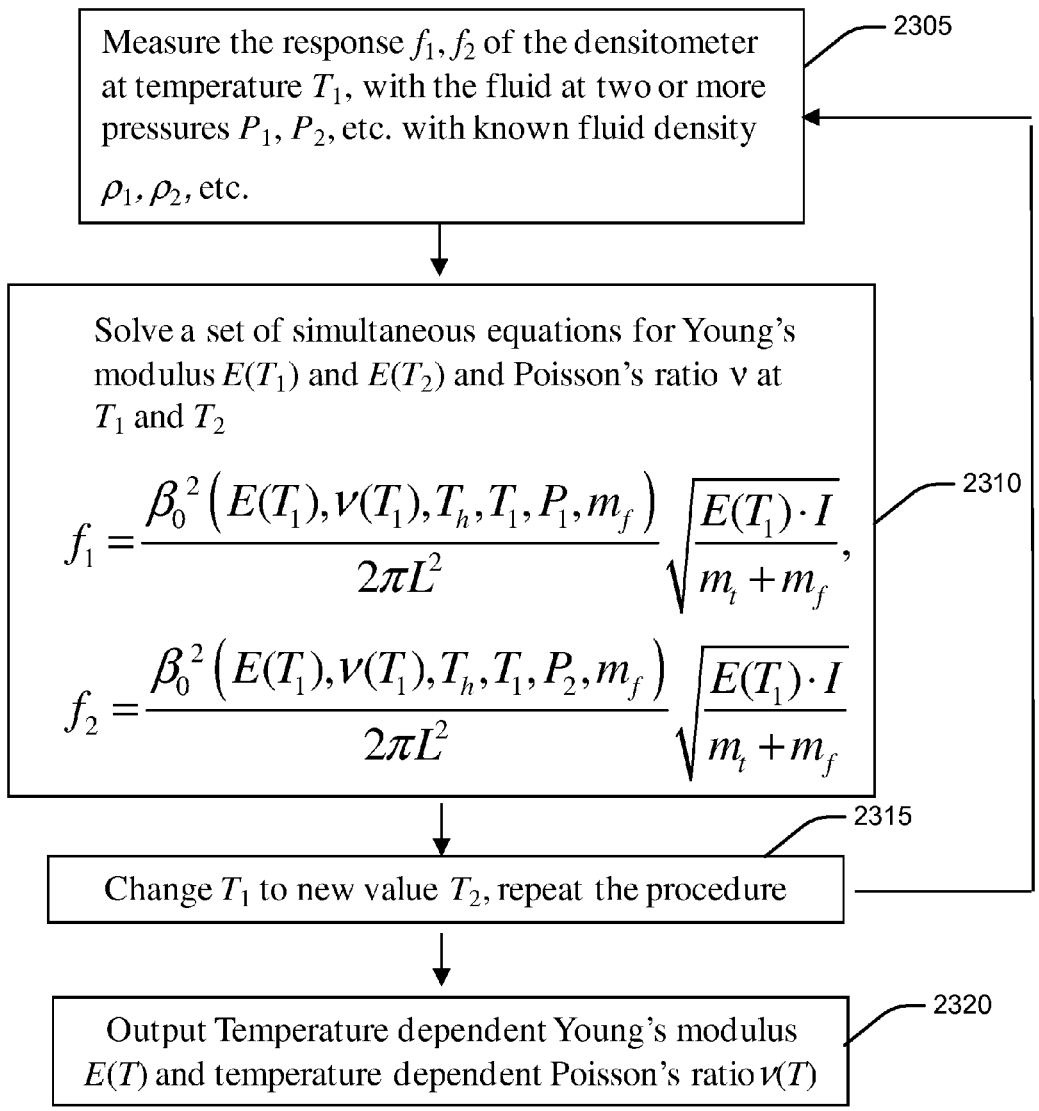

Technique to Obtain the Temperature Dependent Young's Modulus Based on Calibration Measurement Using Simultaneous Solutions at Known Temperatures and Multiple Pressures A technique to obtain the temperature dependent Young's Modulus based on calibration measurement using simultaneous solutions at known temperatures and multiple pressures, illustrated in FIG. 23, begins by measuring the response the response $f_1$, $f_2$ of the densitometer at temperature $T_1$, with the fluid at two or more pressures $P_1$, $P_2$, etc. with known fluid density $\rho_1$, $\rho_2$, etc. (block 2305). The technique next solves a set of simultaneous equations for Young's modulus $E(T_1)$ and $E(T_2)$ and Poisson's ratio v at $T_1$ and $T_2$ using the equations shown in the figure (block 2310). The technique next changes $T_1$ to new value $T_2$ (block 2315) and returns to block 2305. When all of the temperatures have been investigated, the technique outputs the temperature dependent Young's modulus E(T) and temperature dependent Poisson's ratio v(T) (block 2320).

Figure 24:
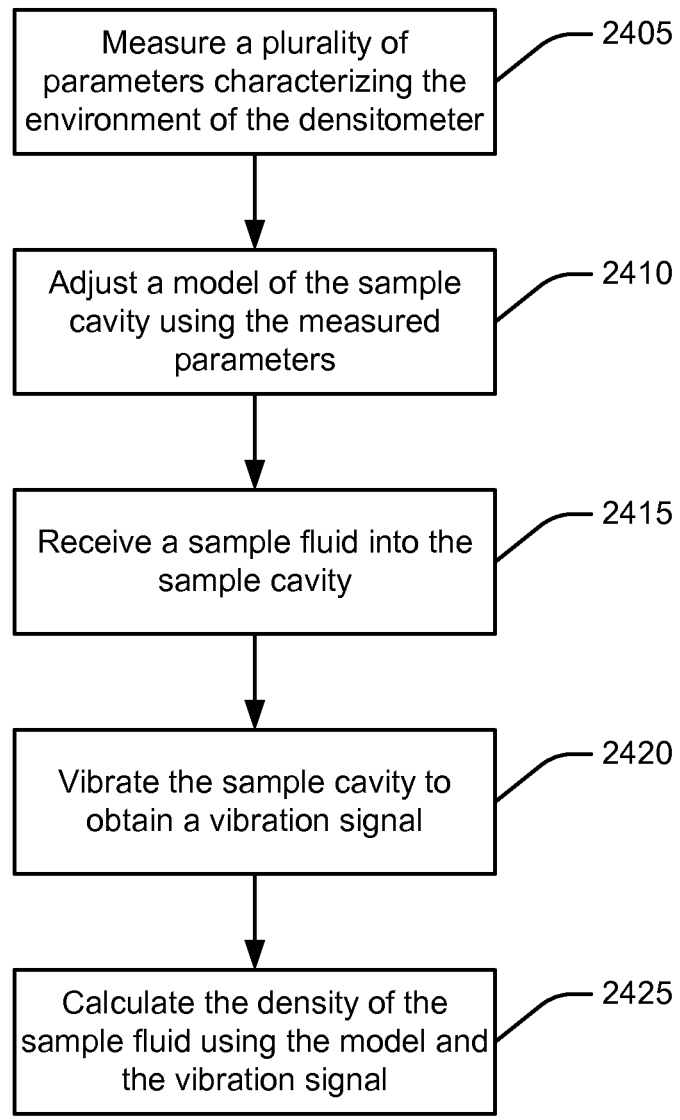
FIG. 24 is a flow chart.

In use, as shown in FIG. 24, the density of a fluid is determined using a vibratory resonant densitometer in an environment. The densitometer includes a tubular sample cavity and other densitometer parts. The technique includes measuring a plurality of parameters characterizing the environment (block 2405). The technique further includes adjusting a model of the sample cavity using the measured parameters (block 2410). The technique further includes receiving a sample fluid into the sample cavity (block 2415). The technique further includes vibrating the sample cavity to obtain a vibration signal (block 2420). The technique further includes calculating the density of the sample fluid using the model and the vibration signal (block 2425).

Figure 25:
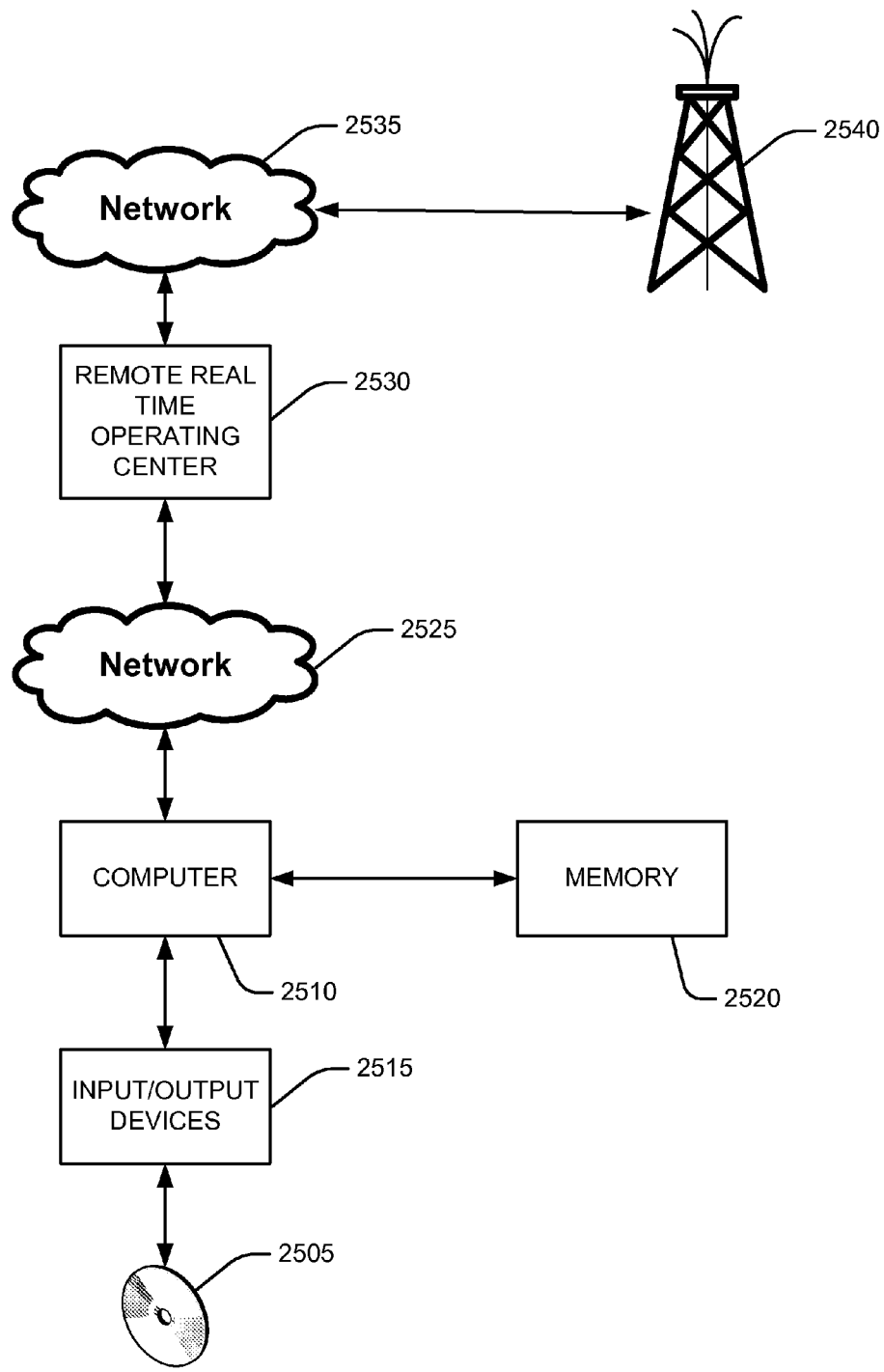
FIG. 25 is a block diagram.

In one embodiment, a computer program for controlling the operation of the acoustic logging tool and for performing analysis of the data collected by the acoustic logging tool is stored on a computer readable media 2505, such as a CD or DVD, as shown in FIG. 25. In one embodiment a computer 2510, which may be the on the surface or which may be the same as system controller 414, reads the computer program from the computer readable media 2505 through an input/output device 2515 and stores it in a memory 2520 where it is prepared for execution through compiling and linking, if necessary, and then executed. In one embodiment, the system accepts inputs through an input/output device 2515, such as a keyboard, and provides outputs through an input/output device 2515, such as a monitor or printer. In one embodiment, the system stores the results of calculations in memory 2520 or modifies such calculations that already exist in memory 2520.

In one embodiment, the results of calculations that reside in memory 2520 are made available through a network 2525 to a remote real time operating center 2530. In one embodiment, the remote real time operating center makes the results of calculations available through a network 2535 to help in the planning of oil wells 2540 or in the drilling of oil wells 2540. Similarly, in one embodiment, the acoustic logging tool 200 can be controlled from the remote real time operating center 2530.

Figure 26:
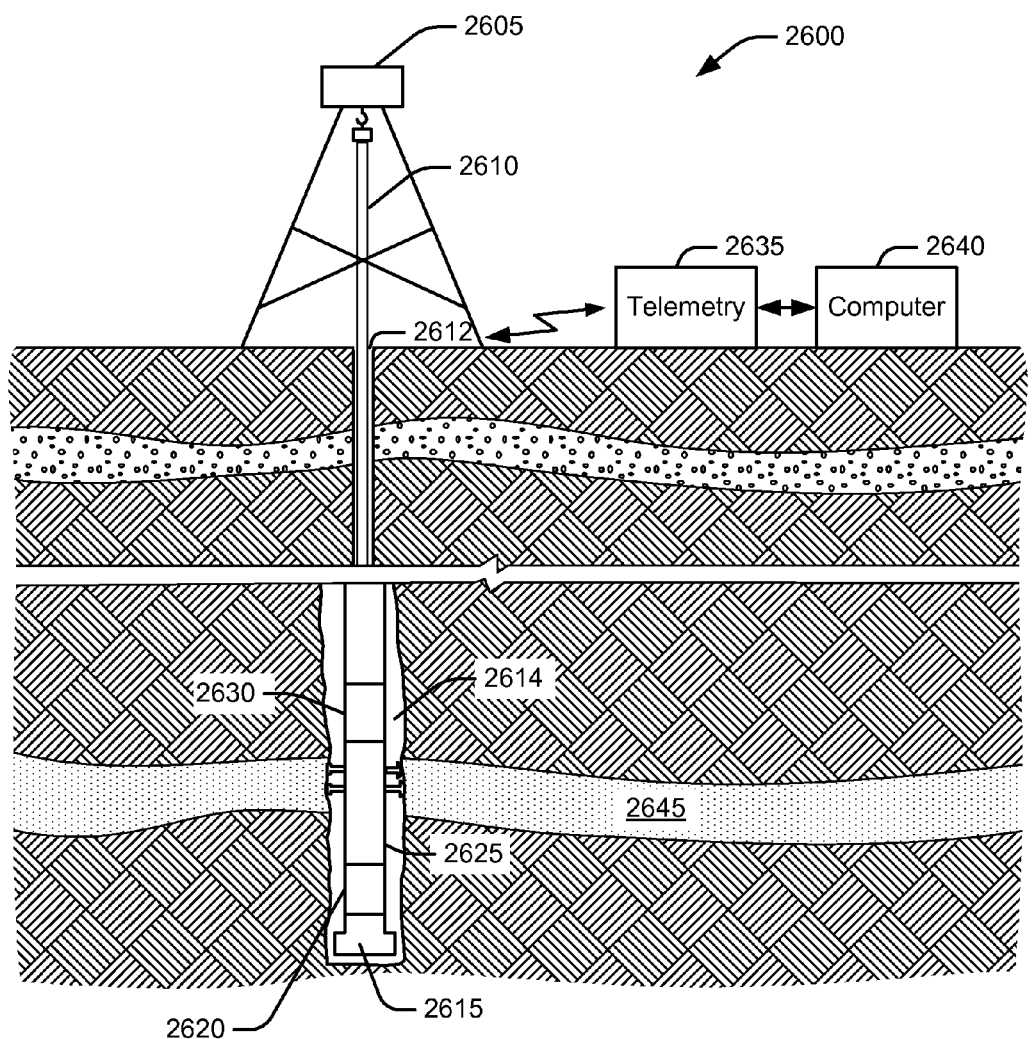
FIG. 26 is a block diagram of an MWD/LWD system.

An example environment 2600, illustrated in FIG. 26, includes a derrick 2605 from which a drill string 2610 is suspended in a borehole 2612. FIG. 26 is greatly simplified and for clarity does not show many of the elements that are used in the drilling process. In one embodiment, the volume within the borehole 2612 around the drill string 2610 is called the annulus 2614. In one embodiment, the drill string includes a bit 2615, a variety of actuators and sensors, shown schematically by element 2620, a instrument 2625, which may be a densitometer such as that illustrated in FIGS. 1-3, used to sense parameters of formation 2645, and a telemetry section 2630, through which the downhole equipment communicates with a surface telemetry system 2635. In one embodiment, a computer 2640, which in one embodiment includes input/output devices, memory, storage, and network communication equipment, including equipment necessary to connect to the Internet, receives data from the downhole equipment and sends commands to the downhole equipment.

The equipment and techniques described herein are also useful in a wireline or slickline environment. In one embodiment, for example, a formation testing tool may be lowered into the borehole 2612 using wired drillpipe, wireline, coiled tubing (wired or unwired), or slickline. In one embodiment of a measurement-while-drilling or logging-while-drilling environment, such as that shown in FIG. 26, power for the formation testing tool is provided by a battery, by a mud turbine, or through a wired pipe from the surface, or through some other conventional means. In one embodiment of a wireline or slickline environment, power is provided by a battery or by power provided from the surface through the wired drillpipe, wireline, coiled tubing, or slickline, or through some other conventional means.

Figure 27:
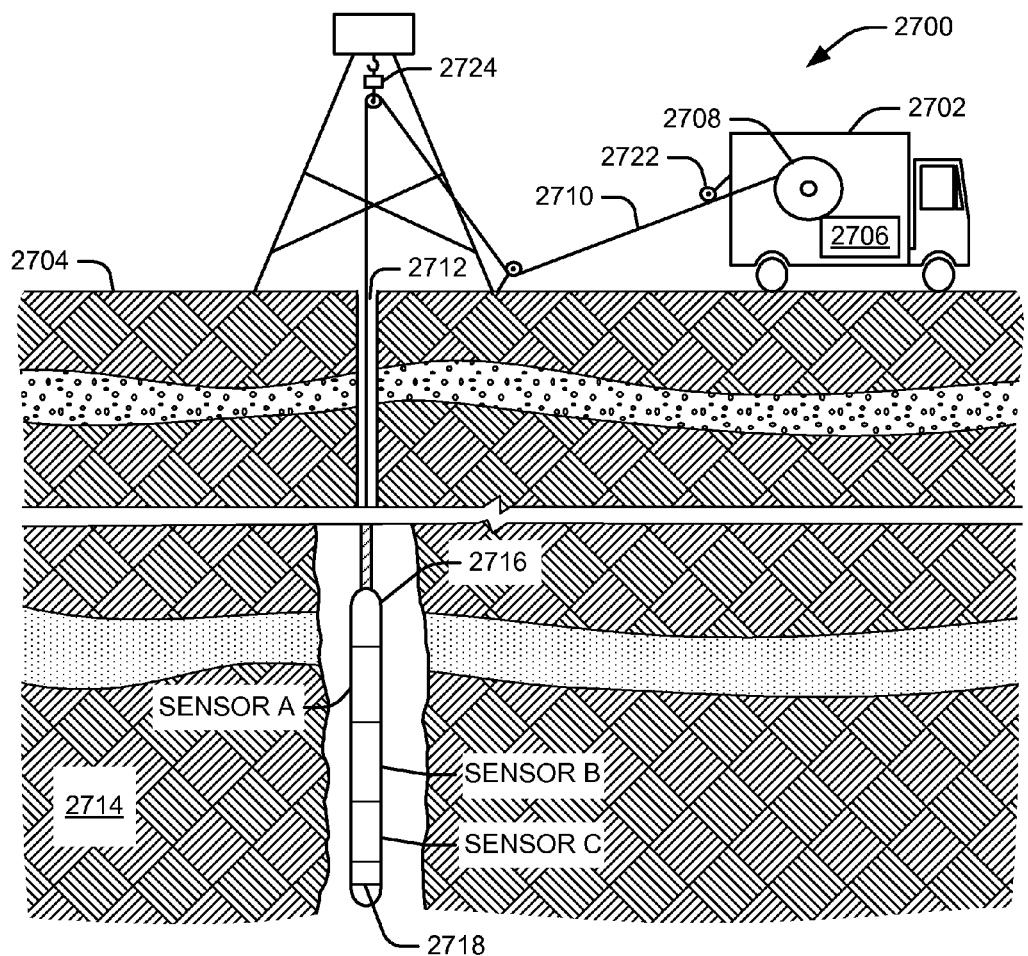
FIG. 27 is a block diagram of a wireline system.

In a typical wireline well logging system at a drilling rig site 2700, as depicted in FIG. 27, a logging truck or skid 2702 on the earth's surface 2704 houses a data gathering computer 2706 and a winch 2708 from which a wireline cable 2710 extends into a well bore 2712 drilled into a hydrocarbon formation 2714. The wireline 2710 suspends a logging toolstring 2716 within the well bore 2712 to measure formation data as the logging tool 2716 is raised or lowered by the wireline 2710. The logging toolstring 2716 includes an instrument 2718, which may be a densitometer such as that illustrated in FIGS. 1-3, and several sensors A, B, C. These sensors may be in different physical entities, called tools, that are screwed together to form the toolstring. Also, one tool may contain several sensors at different lengths along the axis of the tool.

As the logging tool 2716 is raised or lowered within the well bore 2712, a depth encoder 2722 provides a measured depth of the extended cable. A tension load cell 2724 measures tension in the wireline 2710 at the surface 2704.

The equipment and techniques described herein are also useful in a logging while drilling (LWD) or measurement while drilling (MWD) environment. They can also be applicable in cased-hole logging and production logging environment to determine fluid or gas density. In general, the equipment and techniques can be used in situations where the in-situ determination of the density of flowing liquid or gas is highly desirable.

The text above describes one or more specific embodiments of a broader invention. The invention also is carried out in a variety of alternate embodiments and thus is not limited to those described here. The foregoing description of the preferred embodiment of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

What is claimed is:

1. A method for determining the density of a fluid using a vibratory resonant densitometer in an environment, the densitometer including a sample cavity and other densitometer parts, the method comprising:
   measuring, at a time the density of the fluid is to be determined, a plurality of parameters characterizing the environment, the plurality of parameters comprising the temperature of the sample cavity;
   adjusting, at the time the density of the fluid is to be determined, a model of the sample cavity using the measured parameters, the model including the temperature dependent Young's modulus of a material used to make the sample cavity, and adjusting the model of the sample cavity comprising calculating the temperature dependent Young's modulus of the material used to make the sample cavity using the measured temperature of the sample cavity;
   receiving a sample of the fluid into the sample cavity;
   vibrating the sample cavity to obtain a vibration signal; and
   calculating the density of the sample fluid using the model and the vibration signal.

2. The method of claim 1 wherein the plurality of parameters further comprises the fluid pressure in the sample cavity and the model further comprises the fluid pressure in the sample cavity.

3. The method of claim 1 wherein the model comprises solving the following equation for $\rho_f$:

$$f_0 = \frac{\beta_0^2}{2\pi L^2} \sqrt{\frac{E(T_t) \cdot I(T_t)}{m_t + m_f}}$$

where:
   $f_o$ is the resonant frequency of the sample cavity with a fluid having density $\rho_f$ at pressure P and temperature $T_t$ and a sample cavity housing at temperature $T_h$;

$$m_t = \rho_t \cdot \frac{\pi}{4}[a^2(P) - b^2(P)]$$

is the linear density of the sample cavity;

$$m_f = \rho_f \cdot \frac{\pi}{4} b^2(P)$$

is the linear density of the fluid;
   $E(T_t)$ is the temperature dependent Young's modulus of the material used to make the sample cavity;
   $I(T_t)$ is the temperature dependent area moment of inertia of the sample cavity;
   a is the outer diameter of the sample cavity;
   b is the inner diameter of the sample cavity;
   $\rho_t$ is the density of a material from which the sample cavity is made;
   $\rho_f$ is the density of the fluid; and
   $\beta_o$ is a variable that depends on the physical parameters of the densitometer.

4. The method of claim 3 wherein solving the equation comprises:
   (a) measuring the resonant frequency of the sample cavity;
   (b) guessing the value of the fluid density;
   (c) computing the resonant frequency using the equation, the guessed value of fluid density, and measured values of pressure and temperature;
   (d) if the computed resonant frequency matches the measured resonant frequency using the guessed fluid density;
   (e) otherwise, modifying the guessed fluid density and returning to (c).

5. The method of claim 3 wherein solving the equation comprises:
   using a look-up table of $f_o$, $\rho$, P, $T_t$, and $T_h$ created by solving the equation for $f_o$ using combinations of values of $\rho$, P, $T_t$, and $T_h$.

6. The method of claim 3 wherein solving the equation comprises using numerical methods.

7. A computer program, stored on a non-transitory computer-readable tangible medium, for determining the density of a fluid using a vibratory resonant densitometer in an environment, the densitometer including a sample cavity and other densitometer parts, the computer program comprising executable instructions that cause a computer to:
measure, at a time the density of the fluid is to be determined, a plurality of parameters characterizing the environment, the plurality of parameters comprising the temperature of the sample cavity;
adjust, at the time the density of the fluid is to be determined, a model of the sample cavity using the measured parameters, the model including the temperature dependent Young's modulus of a material used to make the sample cavity, and adjusting the model of the sample cavity comprising calculating the temperature dependent Young's modulus of the material used to make the sample cavity using the measured temperature of the sample cavity;
receive a sample of the fluid into the sample cavity;
vibrate the sample cavity to obtain a vibration signal; and
calculate the density of the sample fluid using the model and the vibration signal.

8. The computer program of claim 7 wherein the plurality of parameters further comprises the fluid pressure in the sample cavity and the model further includes the fluid pressure in the sample cavity.

9. The computer program of claim 7 wherein the model comprises solving the following equation for $\rho_f$:

$$f_0 = \frac{\beta_0^2}{2\pi L^2} \sqrt{\frac{E(T_t) \cdot I(T_t)}{m_t + m_f}}$$

where:
$f_o$ is the resonant frequency of the sample cavity with a fluid having density $\rho_f$ at pressure P and temperature $T_t$ and a sample cavity housing at temperature $T_h$;

$$m_t = \rho_t \cdot \frac{\pi}{4}[a^2(P) - b^2(P)]$$

is the linear density of the sample cavity;

$$m_f = \rho_f \cdot \frac{\pi}{4} b^2(P)$$

is the linear density of the fluid;
$E(T_t)$ is the temperature dependent Young's modulus of the material used to make the sample cavity;
$I(T_t)$ is the temperature dependent area moment of inertia of the sample cavity;
a is the outer diameter of the sample cavity;
b is the inner diameter of the sample cavity;
$\rho_t$ is the density of a material from which the sample cavity is made;
$\rho_f$ is the density of the fluid; and
$\beta_o$ is a variable that depends on the physical parameters of the densitometer.

10. The computer program of claim 9 wherein, when solving the equation, the computer:
(a) measures the resonant frequency of the sample cavity;
(b) guesses the value of the fluid density;
(c) computes the resonant frequency using the equation, the guessed value of fluid density, and measured values of pressure and temperature;
(d) if the computed resonant frequency matches the measured resonant frequency using the guessed fluid density;
(e) otherwise, modifying the guessed fluid density and returning to (c).

11. The computer program of claim 9 wherein, when solving the equation, the computer:
using a look-up table of $f_o$, $\rho$, P, $T_t$, and $T_h$ created by solving the equation for $f_o$ using combinations of values of $\rho$, P, $T_t$, and $T_h$.

12. The computer program of claim 9 wherein, when solving the equation, the computer uses numerical methods.

13. A method for measuring a property of a substance using a device operating in an environment, the method comprising:
calculating a temperature dependent Young's modulus for a material used to make a sample cavity within the device using:
data concerning the device; and
data concerning the environment, the data including the temperature of the sample cavity at the time the property is to be measured;
inserting the calculated temperature dependent Young's modulus into a model of the device;
calculating a value for the property using:
the model of the device; and
data regarding the substance.

14. The method of claim 13 wherein the device is a densitometer and calculating the Young's modulus comprises:
measuring the response f of the densitometer at known conditions with known fluid density;
making two initial guesses of Young's modulus: $E_1$ and $E_2$;
solving the following frequency equation for $\beta$:

$$2\varepsilon_1^7 \varepsilon_2^3 \cos(\varepsilon_1) + 4\varepsilon_1^5 \varepsilon_2^5 \cos(\varepsilon_1) + 2\varepsilon_1^3 \varepsilon_2^7 \cos(\varepsilon_1) - 2\varepsilon_1^7 \varepsilon_2^3 \cosh(\varepsilon_2) -$$

$$4\varepsilon_1^5 \varepsilon_2^5 \cosh(\varepsilon_2) + \ldots + (\beta L)^8 \alpha_1 \alpha_2 \varepsilon_1^3 \varepsilon_2 \cos(\varepsilon_1) \sinh(\varepsilon_2) \sinh(\varepsilon_2 \xi_1)$$

$$\sinh[\varepsilon_2(\xi_2 - \xi_1)]\sinh[\varepsilon_2(1 - \xi_2)] + (\beta L)^8 \alpha_1 \alpha_2 \varepsilon_1^3 \varepsilon_2 \cosh(\varepsilon_2)$$

$$\sinh(\varepsilon_2)\sinh(\varepsilon_2 \xi_1)\sinh[\varepsilon_2(\xi_2 - \xi_1)]\sinh[\varepsilon_2(1 - \xi_2)] = 0$$

where:

$$\xi_{1,2} = \frac{x_{1,2}}{L},$$

$$\alpha_{1,2} = \frac{M_{1,2}}{(m_t + m_f) \cdot L},$$

$$\varepsilon_1 = L\sqrt{\frac{B}{2} + \frac{1}{2}\sqrt{B^2 + 4\beta^2}},$$

$$\varepsilon_2 = L\sqrt{-\frac{B}{2} + \frac{1}{2}\sqrt{B^2 + 4\beta^2}},$$

$$B = \frac{\pi}{4}\left[b^3(P)P\left(1 - \frac{2\nu}{1+\eta}\right) + \frac{\alpha E(T)}{1+\eta}[a^2(P) - b^2(P)](T_h - T_t)\right]$$

L=length of the sample cavity;
calculating theoretical frequencies $f_1$ and $f_2$ at $E_1$ and $E_2$ using the following equation:

$$f_{1,2} = \frac{\beta^2}{2\pi L^2}\sqrt{\frac{E_{1,2} \cdot I}{m_t + m_f}}$$

updating E using the following formula:

$$E_3 = E_2 - (E_2 - E_1)\frac{f - f_2}{f_1 - f_2}$$

determining that a stop criterion has been reached; and outputting $E_3$ as Young's modulus.

15. The method of claim 13 wherein the device is a densitometer and calculating the temperature dependent Young's modulus comprises:
  measuring the response f of the densitometer at known conditions with known fluid density;
  assuming a constant Young's modulus value $E_o$;
  solving the following equation for $\beta$:

$$2\varepsilon_1^7\varepsilon_2^3\cos(\varepsilon_1) + 4\varepsilon_1^5\varepsilon_2^5\cos(\varepsilon_1) + 2\varepsilon_1^3\varepsilon_2^7\cos(\varepsilon_1) - 2\varepsilon_1^7\varepsilon_2^3\cosh(\varepsilon_2) -$$
$$4\varepsilon_1^5\varepsilon_2^5\cosh(\varepsilon_2) + \ldots + (\beta L)^8\alpha_1\alpha_2\varepsilon_1^3\varepsilon_2\cos(\varepsilon_1)\sinh(\varepsilon_2)\sinh(\varepsilon_2\xi_1)$$
$$\sinh[\varepsilon_2(\xi_2 - \xi_1)]\sinh[\varepsilon_2(1-\xi_2)] + (\beta L)^8\alpha_1\alpha_2\varepsilon_1^3\varepsilon_2\cosh(\varepsilon_2)$$
$$\sinh(\varepsilon_2)\sinh(\varepsilon_2\xi_1)\sinh[\varepsilon_2(\xi_2 - \xi_1)]\sinh[\varepsilon_2(1-\xi_2)] = 0$$

where:

$$\xi_{1,2} = \frac{x_{1,2}}{L},$$

$$\alpha_{1,2} = \frac{M_{1,2}}{(m_t + m_f) \cdot L},$$

$$\varepsilon_1 = L\sqrt{\frac{B}{2} + \frac{1}{2}\sqrt{B^2 + 4\beta^2}},$$

$$\varepsilon_2 = L\sqrt{-\frac{B}{2} + \frac{1}{2}\sqrt{B^2 + 4\beta^2}},$$

$$B = \frac{\pi}{4}\left[b^3(P)P\left(1 - \frac{2\nu}{1+\eta}\right) + \frac{\alpha E(T)}{1+\eta}[a^2(P) - b^2(P)](T_h - T_t)\right]$$

L=length of the sample cavity;
calculating a theoretical frequency $f_o$ using the following equation:

$$f_0 = \frac{\beta_0^2}{2\pi L^2}\sqrt{\frac{E_0 \cdot I}{m_t + m_f}}$$

calculating a ratio of the square of the measured frequency $f^2$ to the square of the calculated frequency $f_0^2$;
using a regression analysis to obtain the coefficients $\alpha_0$, $\alpha_1$, $\alpha_2$, ... in the following equation:

$$\frac{f^2}{f_0^2} = (a_0 + a_1 T_t + a_2 T_t^2 + a_3 T_t^3 + \ldots)$$

calculating the temperature dependent Young's modulus using the following equation:

$$E(T) = E_o(\alpha_o + \alpha_1 T_t + \alpha_2 T_t^2 + \alpha_3 T_t^3 + \ldots).$$

16. The method of claim 13 wherein the device is a densitometer and calculating the Young's modulus comprises:
  (a) measuring the responses $f_1$, $f_2$ of the densitometer at temperature $T_1$, with the fluid at two or more pressures $P_1$, $P_2$, etc. with known fluid density $\rho_1$, $\rho_2$,
  (b) solving a set of simultaneous equations for Young's modulus $E(T_1)$ and Poisson's ratio $\nu(T_1)$ at $T_1$ using the following equations:

$$f_1 = \frac{\beta_0^2(E(T_1), \nu(T_1), T_h, T_1, P_1, m_f)}{2\pi L^2}\sqrt{\frac{E(T_1) \cdot I}{m_t + m_f}},$$

$\beta_0$ calculated at $T_1$, $P_1$;

$$f_1 = \frac{\beta_0^2(E(T_1), \nu(T_1), T_h, T_1, P_2, m_f)}{2\pi L^2}\sqrt{\frac{E(T_1) \cdot I}{m_t + m_f}},$$

$\beta_0$ calculated at $T_1$, $P_2$;
  (c) changing $T_1$ to new value $T_2$ and returning to (a);
  (d) determining that all of the temperatures have been investigated and, in response, outputting the temperature dependent Young's modulus E(T) and temperature dependent Poisson's ratio $\nu(T)$.

17. The method of claim 13 further comprising inserting a fluid pressure in the sample cavity at the time the property is to be measured into the model of the device.

* * * * *